(12) United States Patent
Lejeune et al.

(10) Patent No.: US 10,244,692 B2
(45) Date of Patent: Apr. 2, 2019

(54) METHOD OF IMPROVED PLANT BREEDING

(71) Applicant: BASF Plant Science GmbH, Ludwigshafen (DE)

(72) Inventors: Pierre Lejeune, Dolembreux (BE); Frederik Leyns, Oosterzele (BE); Cedrick Vandaele, Ghent (BE); Wim Van Caeneghem, Brakel (BE)

(73) Assignee: BASF Plan Science GmbH, Ludwigshafen (DE)

( * ) Notice: Subject to any disclaimer, the term of this patent is extended or adjusted under 35 U.S.C. 154(b) by 633 days.

(21) Appl. No.: 14/624,796

(22) Filed: Feb. 18, 2015

(65) Prior Publication Data

US 2015/0223419 A1 Aug. 13, 2015

Related U.S. Application Data

(62) Division of application No. 13/063,217, filed as application No. PCT/EP2009/061985 on Sep. 16, 2009, now Pat. No. 8,991,098.

(Continued)

(30) Foreign Application Priority Data

Dec. 23, 2008 (EP) .................... 08172858

(51) Int. Cl.
*A01G 9/08* (2006.01)
*A01H 1/04* (2006.01)
(Continued)

(52) U.S. Cl.
CPC ............. *A01H 1/04* (2013.01); *A01G 9/02* (2013.01); *B65G 15/005* (2013.01); *B65G 15/14* (2013.01);
(Continued)

(58) Field of Classification Search
CPC ........... A01G 9/00; A01G 9/088; A01G 9/108
See application file for complete search history.

(56) References Cited

U.S. PATENT DOCUMENTS 2,244,677 A 6/1941 Cornell
3,063,195 A 11/1962 Ravich
(Continued)

FOREIGN PATENT DOCUMENTS

DE 39 06 215 A1 8/1990
DE 42 00 001 A1 7/1993
(Continued)

OTHER PUBLICATIONS

Boyes, D.C., et al., "Growth Stage-Based Phenotypic Analysis of *Arabidopsis*: A Model for High Throughput Functional Genomics in Plants", The Plant Cell, 2001, vol. 13, pp. 1499-1510.
(Continued)

*Primary Examiner* — Kristen C Hayes

(57) ABSTRACT

An improved plant breeding system for high throughput analysis of plant phenotype and genotype is provided. A method for analyzing the impact of genetic modifications on plants and selecting a plant with a genetic modification of interest is also provided. Also provided is a method for developing marketable information for improved plant breeding and a method for collecting data on a selected plant phenotype for rapid analysis of the effect of a genetic modification on the selected phenotype.

22 Claims, 10 Drawing Sheets

US 10,244,692 B2

Page 2

Related U.S. Application Data

(60) Provisional application No. 61/097,222, filed on Sep. 16, 2008.

(51) Int. Cl.
  *B65G 15/00* (2006.01)
  *B65G 15/14* (2006.01)
  *A01G 9/02* (2018.01)
  *B65G 43/00* (2006.01)
  *G05B 15/02* (2006.01)
  *G06T 7/00* (2017.01)

(52) U.S. Cl.
  CPC ............ *B65G 43/00* (2013.01); *G05B 15/02* (2013.01); *G06T 7/0012* (2013.01); *G06T 2207/30188* (2013.01)

(56) References Cited

U.S. PATENT DOCUMENTS

| | | | | |
|---|---|---|---|---|
| 3,771,258 A | * | 11/1973 | Charney | A01G 31/042 104/25 |
| 3,824,736 A | | 7/1974 | Davis | |
| 4,015,366 A | | 4/1977 | Hall, III | |
| 4,028,847 A | | 6/1977 | Davis et al. | |
| 4,035,949 A | | 7/1977 | Ruthner | |
| 4,454,806 A | | 6/1984 | Schultz | |
| 4,481,893 A | | 11/1984 | Qvarnström | |
| 4,570,380 A | | 2/1986 | Ray et al. | |
| 4,628,631 A | | 12/1986 | Van Wingerden | |
| 4,750,035 A | | 6/1988 | Chang et al. | |
| 4,950,166 A | | 8/1990 | Williams | |
| 5,013,658 A | | 5/1991 | Dooner et al. | |
| 5,247,761 A | | 9/1993 | Miles et al. | |
| 5,253,302 A | | 10/1993 | Massen | |
| 5,303,505 A | * | 4/1994 | Sumiyoshi | A01G 9/143 47/65 |
| 5,394,646 A | * | 3/1995 | Sumiyoshi | A01G 9/143 47/17 |
| 5,523,231 A | | 6/1996 | Reeve | |
| 5,536,901 A | | 7/1996 | Greaves et al. | |
| 5,561,943 A | * | 10/1996 | Valstar | A01G 31/042 47/39 |
| 5,710,367 A | | 1/1998 | Kindiger et al. | |
| 5,723,596 A | | 3/1998 | Cramer et al. | |
| 5,735,077 A | | 4/1998 | Warfield, Jr. | |
| 5,741,684 A | | 4/1998 | Fabijanski et al. | |
| 5,750,386 A | | 5/1998 | Conkling et al. | |
| 5,764,819 A | | 6/1998 | Orr et al. | |
| 5,780,709 A | | 7/1998 | Adams et al. | |
| 5,864,984 A | | 2/1999 | McNertney | |
| 5,878,527 A | * | 3/1999 | Valstar | A01G 31/042 47/62 C |
| 5,941,019 A | | 8/1999 | Guarriello, Sr. et al. | |
| 5,943,818 A | | 8/1999 | Fruehwirth | |
| 6,164,537 A | | 12/2000 | Mariani et al. | |
| 6,230,440 B1 | | 5/2001 | Deutsch | |
| 6,247,269 B1 | | 6/2001 | Valiquette | |
| 6,298,598 B1 | | 10/2001 | Wach et al. | |
| 6,483,434 B1 | | 11/2002 | UmiKer | |
| 6,505,425 B1 | | 1/2003 | Gilbert | |
| 6,506,964 B1 | | 1/2003 | Carolo | |
| 6,646,264 B1 | | 11/2003 | Modiano et al. | |
| 6,701,665 B1 | | 3/2004 | Ton et al. | |
| 6,706,989 B2 | | 3/2004 | Hunter et al. | |
| 6,745,127 B2 | | 6/2004 | Crosby | |
| 6,882,740 B1 | | 4/2005 | McDonald, Jr. et al. | |
| 7,278,236 B2 | | 10/2007 | McDonald et al. | |
| 7,367,458 B2 | | 5/2008 | Leyns et al. | |
| 7,403,855 B2 | | 7/2008 | Fuessley et al. | |
| 7,506,472 B2 | * | 3/2009 | Leyns | A01G 9/143 47/1.01 Pke |
| 7,665,244 B2 | * | 2/2010 | Jesness, III | A01G 27/006 47/39 |
| 7,697,133 B2 | * | 4/2010 | Leyns | A01G 9/143 356/300 |
| 7,845,111 B2 | * | 12/2010 | Dillen | A01G 9/143 47/58.1 R |
| 7,866,091 B2 | | 1/2011 | Dillen et al. | |
| 8,205,789 B2 | * | 6/2012 | Mori | A01G 9/143 111/200 |
| 8,209,903 B2 | * | 7/2012 | Dillen | A01G 9/143 47/58.1 R |
| 8,371,459 B1 | | 2/2013 | Rekhels | |
| 8,559,679 B2 | * | 10/2013 | Lejeune | A01G 1/00 241/7 |
| 8,670,594 B2 | * | 3/2014 | Lejeune | A01G 1/00 241/7 |
| 2002/0066418 A1 | | 6/2002 | Fearing et al. | |
| 2002/0144458 A1 | | 10/2002 | Hunter et al. | |
| 2003/0061763 A1 | | 4/2003 | Weder et al. | |
| 2003/0126791 A1 | | 7/2003 | Weder | |
| 2003/0174046 A1 | | 9/2003 | Abrams | |
| 2003/0221212 A1 | | 11/2003 | Tomes et al. | |
| 2004/0088916 A1 | | 5/2004 | Ton et al. | |
| 2004/0122592 A1 | | 6/2004 | Fuessley et al. | |
| 2004/0163308 A1 | | 8/2004 | Uchiyama | |
| 2004/0200145 A1 | | 10/2004 | Egan | |
| 2004/0200146 A1 | * | 10/2004 | Leyns | A01G 9/143 47/65 |
| 2004/0201454 A1 | | 10/2004 | Waterhouse et al. | |
| 2005/0108608 A1 | | 5/2005 | Chee Hong | |
| 2006/0150490 A1 | * | 7/2006 | Dillen | A01G 9/143 47/58.1 R |
| 2007/0186313 A1 | | 8/2007 | Lightner et al. | |
| 2007/0289211 A1 | * | 12/2007 | Lejeune | A01G 1/00 47/65 |
| 2008/0297790 A1 | | 12/2008 | Leyns et al. | |
| 2009/0035782 A1 | * | 2/2009 | Dillen | A01G 9/143 435/6.12 |
| 2009/0151244 A1 | | 6/2009 | Jesness, III | |
| 2011/0107665 A1 | | 5/2011 | Dillen et al. | |
| 2011/0174873 A1 | * | 7/2011 | Mori | A01G 9/143 235/375 |
| 2012/0124904 A1 | | 5/2012 | Marchildon | |
| 2012/0150341 A1 | | 6/2012 | Leyns et al. | |
| 2012/0247016 A1 | | 10/2012 | Dillen et al. | |

FOREIGN PATENT DOCUMENTS

| | | |
|---|---|---|
| DE | 42 41 950 A1 | 5/1994 |
| DE | 198 45 883 A1 | 5/1999 |
| DE | 199 20 920 A1 | 11/2000 |
| DE | 199 50 532 A1 | 7/2001 |
| EP | 0 302 183 A2 | 2/1989 |
| EP | 0 919 492 A1 | 6/1999 |
| EP | 1 154 370 A2 | 11/2001 |
| EP | 1 157 961 A2 | 11/2001 |
| EP | 1 198 985 A1 | 4/2002 |
| EP | 1 433 377 A1 | 6/2004 |
| EP | 1 862 051 A2 | 12/2007 |
| FR | 2 709 636 A1 | 3/1995 |
| GB | 1 160 512 A | 8/1969 |
| GB | 1 576 010 A | 10/1980 |
| GB | 2 197 574 A | 5/1988 |
| GB | 2 305 839 A | 4/1997 |
| JP | S63-296634 A | 12/1988 |
| JP | H3-251123 A | 11/1991 |
| JP | 10155366 | 6/1998 |
| WO | WO-95/32056 A1 | 11/1995 |
| WO | WO-00/56905 A2 | 9/2000 |
| WO | WO-00/63362 A1 | 10/2000 |
| WO | WO-01/77671 A1 | 10/2001 |
| WO | WO-02/21905 A1 | 3/2002 |
| WO | WO-2004/068934 A2 | 8/2004 |

(56) References Cited

FOREIGN PATENT DOCUMENTS

| WO | WO-2006/029987 A1 | 3/2006 |
|----|-------------------|--------|
| WO | WO-2007/093444 A1 | 8/2007 |

OTHER PUBLICATIONS

CropDesign, Copy of Information from CropDesign's webpage on or around Jul. 31, 2002.

Cullis, B. R., et al., "An Examination of the Efficiency of Australian Crop Variety Evaluation Programmes", Journal of Agricultural Science, 2000, vol. 135, pp. 213-222.

Frensham, A. B., et al., "A Mixed Model Analysis of 10 Years of Oat Evaluation Data: Use of Agronomic Information to Explain Genotype by Environment Interaction", Euphytica, 1998, vol. 99, pp. 43-56.

Granier, C., et al., "Phenopsis, An Automated Platform for Reproducible Phenotyping of Plant Responses to Soil Water Deficit in *Arabidopsis thaliana* Permitted the Identification of an Accession with Low Sensitivity to Soil Water Deficit", New Phytologist, 2006, vol. 169, pp. 623-635.

Heeraman, D. A., et al., "Three Dimensional Imaging of Plant Roots in Situ with X-Ray Computed Tomography", Plant and Soil, 1997, vol. 189, No. 2, pp. 167-179.

International Search Report of PCT/EP2004/050085 dated Aug. 30, 2004.

Lemnatec GMBH: "Lemnatec: Image processing in biology", [Online] Sep. 17, 2007, pp. 1-13, XP002558586.

Lemnatec Gmbh: "Plant Phenotyping 3:31", Youtube—LEMNATEC2008 Channel, [Online] Sep. 15, 2008, pp. 1-12, XP002558584.

Press Release: "Targeted Growth and Crop Design Conclude Research Collaboration and License Agreement", Targeted Growth, Inc., CropDesign N.V., published May 9, 2001, pp. 1-2.

Rigney, M. P., et al., "Machine Vision for Conifer Seedling Quality Control", New Forests, 1996, vol. 13, pp. 51-62.

Vandenhirtz, D., "Get an Impression of Your Plants", 2008 International Meeting on Controlled Environment Agriculture; North American Committee on Controlled Environment Technology and Use (NCERA 101), [Online] Mar. 12, 2008, pp. 1-63, XP002558585.

Wang, Y., et al., "Seeing 'Cool' and 'Hot'—Infrared Thermography as a Tool for Non-Invasive, High-Throughput Screening of *Arabidopsis* Guard Cell Signalling Mutants," Journal of Experimental Botany, 2004, vol. 55, No. 400, pp. 1187-1193.

Yang, Y.-Z., et al., "Review on the Proceeding of Automatic Seedlings Classification by Computer Vision", Journal of Forestry Research, 2002, vol. 13, No. 3, pp. 245-249.

\* cited by examiner

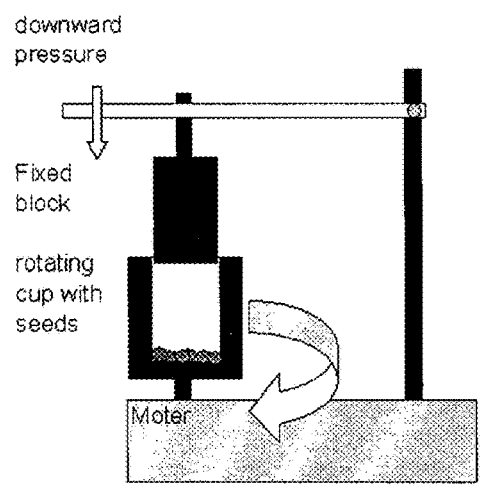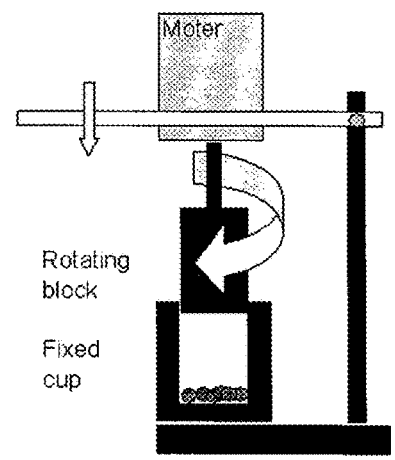
FIGURE 4A                    FIGURE 4B

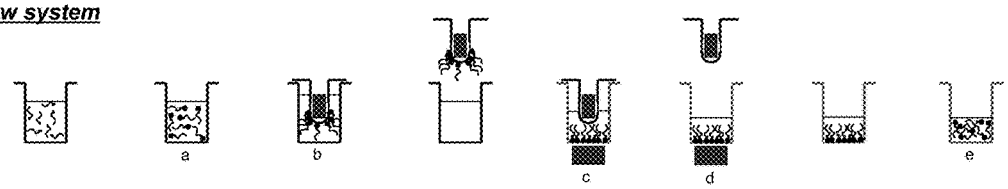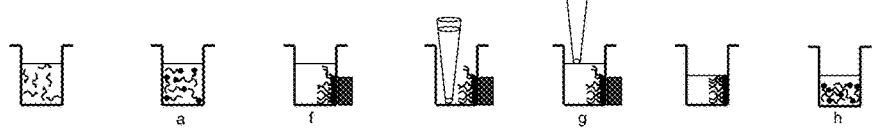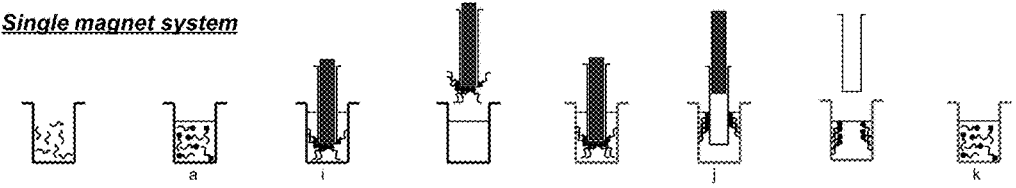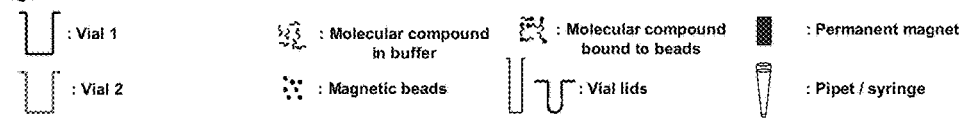
FIGURE 10

METHOD OF IMPROVED PLANT BREEDING

RELATED APPLICATIONS

This application is a divisional application of U.S. application Ser. No. 13/063,217 filed Mar. 10, 2011, now U.S. Pat. No. 8,991,098, issued Mar. 31, 2015, which is a national stage application (under 35 U.S.C. § 371) of PCT/EP2009/061985, filed Sep. 16, 2009, which claims benefit of U.S. Application 61/097,222, filed Sep. 16, 2008 and European Application 08172858.6 filed Dec. 23, 2008 in European Patent Office. The entire contents of each of these applications are hereby incorporated by reference herein in their entirety

FIELD OF THE INVENTION

The invention relates generally to an improved plant breeding system. More particularly, this invention relates to a method for automated, high throughput analysis of plant phenotype and plant genotype in a breeding program.

BACKGROUND OF THE INVENTION

Plant breeding programs require analyses of phenotypes for a large number of plants. These analyses involve measurement of a wide array of plant characteristics including plant morphology, disease and environmental stress tolerance, seed quality, and yield. In addition to the evaluation of phenotype, breeding programs often necessitate determination of genotype, for example, to identify a DNA marker associated with a specific phenotype or to confirm the presence of a transgene in a transgenic plant. Therefore extraction of plant genomic DNA may also be necessary.

Traditionally, analysis of phenotype in a breeding program has been conducted through visual evaluation and manual measurement of morphological characteristics. However, due to the large number of plants that must be evaluated and to the small differences when plants are evaluated early, this process is extremely time consuming, thus limiting the number of plants that can be analyzed. Initial attempts have been made to automate this process by developing evaluation methods for the model plant *Arabidopsis thaliana*. For example, Granier et al. describe a system composed of steel frame supporting trays with holes to support pots and a mechanical arm able to move according to a software program (Granier et al., 2002, New Phytologist 169: 623-635). *Arabidopsis* plants were grown in growth chambers and displacement sensors, a balance, a tube for irrigation and a camera were loaded onto the arm to weigh, irrigate, and take a digital picture of each pot. Boyes et al. describe a high throughput process for phenotypic analysis based on a series of defined growth stages in *Arabidopsis* that serve as developmental landmarks and as triggers for the collection of morphological data. Measurements were made with a caliper or ruler or by visual inspection (Boyes et al., 2001, Plant Cell 13: 1499-1510). Wang et al. describe the use of infrared thermography as a non-invasive, high throughput tool for screening of *Arabidopsis* guard cell signaling mutants (Wang et al., 2004, J. Exp. Bot. 55: 1187-1193).

Although high throughput screening methods have been developed for *Arabidopsis*, the greater size and morphological complexity of crop species limit the adaptability of these methods to breeding programs for crop species. Components of phenotyping systems adaptable to crop species have been developed. For example, U.S. Pat. No. 5,253,302 discloses a method for automatic optical classification of plants in which an image of each plant is captured by a color video camera. U.S. Published Application No. 2005/0180608 discloses a plant growth analysis system using an image acquisition system for phenotype functional analysis. The plant growth analysis system has a mechanism for conveying many observed objects which repeatedly pass a camera. U.S. Published Application No. 2007/0186313 discloses a method for the rapid evaluation of transgene function in maize plants. The method uses quantitative, non-destructive imaging technology to evaluate agronomic traits of interest in a controlled, statistically relevant greenhouse environment. U.S. Pat. No. 7,278,236 discloses an apparatus and method for nondestructively acquiring images of a plant root system. The apparatus includes a substrate for supporting the plant root system, a container for holding the substrate, an x-ray radiation source, and an x-ray image capture system. One critical aspect of plant imaging systems is the ability to turn the plant to capture images from several different angles. Systems exist that turn plants around on a fixed turntable while being photographed. Some systems provide several cameras for photographing plants at different angles. Although methods for turning plants during imaging have been developed, a need still exists for a system in which the plant or the imaging device can be turned with precision while the plant is still moved at high speed.

One of the challenges in a breeding program is to develop a system for identifying and tracking the large number of plants being evaluated. Several tracking systems which could be used for high throughput phenotype screening have been developed. U.S. Pat. No. 6,483,434 discloses a container tracking system comprising a computer system for tracking a plurality of containers or carriers. For the purpose of easily tracking any individual container or carrier, a transponder is disposed on the body of the container or carrier. U.S. Pat. No. 7,403,855 discloses an apparatus and method of tracking individual plants growing and/or taken from a growing location such as a field, growing bed, plot or greenhouse. Machine-readable data related to the individual plants is maintained in close association with the corresponding plant. U.S. Published Application No. 2004/0200146 provides an apparatus for use in conjunction with a container in which one or more plants is growing. The container has associated with it a device for receiving an enquiry signal and automatically responding by transmitting a unique identifier signal. EP1157961 discloses a container identification device which has an interrogation device with a transmitter and receiver unit using a pulse signal for interrogating identification information. This identification information is provided by a ticket attached to the container which acts as a surface wave sensor.

Another challenge in developing a system for automated analysis of plant phenotype is the need for moving large numbers of plants. Systems of moving plants for plant production have been developed. U.S. Pat. No. 5,394,646 discloses a system for automatically cultivating crops which consists of a first structure for conveying seedlings in a first predetermined path to allow seedlings to be treated under a first set of controlled growing conditions, a second structure for conveying seedlings in a second predetermined path to allow the seedlings to be treated under a second set of controlled growing conditions, and a structure for selectively diverting seedlings from the first structure onto the second structure. GB 1576010 provides an apparatus for supporting material or containers in which plants can be grown for movement along a greenhouse. The apparatus comprises at least two spaced apart parallel rails forming a track, a runner mounted on each rail for movement along the rail, and one or more elongate carrier members for supporting the material or containers. One or more carrier members are in the form of a trough extending transversely of the rails and are movable with the runners along the rails. U.S. Pat. No. 3,824,736 discloses a method for continuous plant production by moving plants on a conveyor through a corridor wherein closely controlled conditions of temperature and humidity are maintained. The corridor is formed by a series of modular units which include an illuminated section and a darkened section. Each modular unit is arranged to constitute one 24 hour growth period. U.S. Pat. No. 4,035,949 discloses an installation for rearing plants comprising a plurality of successive, independent culture chambers which include endless circulating support means on which plants are moved through zones in said chambers under controlled environmental conditions. U.S. Pat. No. 4,481,893 discloses an apparatus for use in mass growing of seedlings in a greenhouse for automatically handling seedling units comprising pots. The apparatus examines if each pot has an acceptable seedling and optionally automatically inserts a replacement seedling into any pot which needs a replacement seedling.

In determining plant phenotype, it is critical to minimize environmental variation to ensure that any differences observed among breeding lines are due to genetic variation and not simply caused by environmental effects. In conventional breeding programs, plants are grown in the field in several different locations to expose each genotype to a range of different environmental conditions. Another approach is to grow plants in controlled environments such as greenhouses and growth chambers to provide more uniform environmental conditions. However variations in several parameters, such as temperature and light intensity, often still occur. Although growth of plants in randomized complete blocks can help to mitigate the effects of environmental variation, this approach requires the growth of several plants of each genotype. Instead of minimizing environmental variation across a growing area, it is also possible to provide more uniform growth conditions by moving plants through the growing area. For example, U.S. Published Application No. 2006/0150490 discloses a process for breeding plants which comprises growing plants in an environment of controlled climatic conditions and changing the positions of the containers within the environment as required to ensure at least substantially uniform exposure of all plants in the containers to conditions in the environment.

Another aspect of evaluating plant phenotype is determination of seed quality. Seed quality measurements often require removal of the outer layers of the seed, i.e. dehulling. Development of a seed dehulling apparatus for breeding programs presents particular challenges. Existing seed dehullers work on either large amounts of seed (several kilograms) or very small amounts of seed (10-50 seeds), but breeding programs often require analysis of intermediate amounts of seed (50 to 1000 seeds) which are not easily processed by existing dehullers. Furthermore, breeding programs involve the processing of large numbers of seed lots in which each seed lot has a distinct genotype. Therefore, it is critical not to mix seed from different lots. Conventional dehullers can often trap seed in cavities of the device, allowing for contamination. Finally, since the genetic variation among seed lots can result in seeds of varying size, shape, and hull strength, the seed dehulling apparatus must be able to process a wide range of seed without causing damage. Many existing seed dehullers contain rubber rolls or concave disks with an abrasive coating (as described, for example, in U.S. Pat. No. 4,454,806) for removal of the hull. The curved surfaces of these devices can lead to breakage, especially for long, thin seeds. The seed dehullers can also be incorporated into a system for sorting and processing of seed. For example, U.S. Pat. No. 6,706,989 discloses a method and apparatus for processing seed or seed samples including an autonomous sorter which sorts seed by preprogrammed criteria. Optional features can include a counter, a cleaning device, a sheller, and a label applicator.

As mentioned above, extraction of DNA from plant tissue is often necessary in a breeding program for analysis of genotype. WO 00/63362 discloses a method for the extraction of DNA from plants. The method isolates DNA using immobilized anionic groups, preferably on a chromatographic substrate or more preferably magnetic beads derivatized with anionic groups such as diethylaminoethyl (DEAE) via an anion-exchange interaction. U.S. Pat. No. 5,523,231 discloses a method of recovering a biopolymer, including DNA, from solution involving the use of magnetically attractable beads which do not specifically bind the polymer. The beads are suspended in solution and the polymer is precipitated out of solution and becomes nonspecifically associated with the beads.

When the beads are magnetically drawn down the polymer is drawn down with them. The polymer can subsequently be re-dissolved and separated from the beads.

Plant breeding requires several distinct steps, including assessment of plant growth and morphology, processing of seed lots, and genetic analysis of plant tissue. Although initial advances toward automating these individual steps have been made, there is still a need to overcome the obstacles and solve problems in order to integrate these components into a highly automated, high throughput system for phenotypic and genetic analysis of crop species.

SUMMARY OF THE INVENTION

The present invention relates to a method for analyzing the impact of genetic modifications on plants and selecting a plant with a genetic modification of interest. In one aspect, the method comprises
  (a) providing a plurality of plants growing under controlled environmental conditions, each plant being associated with a machine-readable identification that distinguishes the plant from other plants;
  (b) moving the plants in an automated transporter system at one or more intervals during their growing cycle so as to avoid extended exposure to a particular microenvironment, thereby reducing the influence of microenvironment variations on the phenotype of the plants;
  (c) transporting one or more plants at one or more intervals during its growing cycle through a continuous system for imaging of the plant, wherein the system for imaging comprises a turning mechanism and an imaging device, wherein the plants are being turned and imaged in a controlled manner or the imaging device is moved to image the plant in a controlled manner;
  (d) imaging one or more characteristic of the plant while the plant is being moved through the imaging system;
  (e) analyzing the images for the one or more characteristic of the plant by computer processing and associating the resulting information with the machine-readable identification information for the plant;
  (f) analyzing the resulting information for the one or more characteristic of the one or more plant to determine the impact of the genetic modification; and (g) either selecting one or more plants with a genetic modification of interest or communicating information from analyzing steps e) and/or f) to others for selecting one or more plants with a genetic modification of interest.

In one embodiment, the turning mechanism used in the method comprises time-belts, wherein the time-belts and/or the containers are coated with a high friction material. The time-belts are positioned in order to grip the sides of the container and may have different speed settings allowing the container to turn in a controlled way while being transported over the belts.

In one embodiment, the imaging system comprises one or more high speed and/or high resolution cameras.

In another aspect, the invention relates to a plant breeding system for high throughput analysis of genetic traits in plants, which comprises
  (a) an array of containers charged with growing medium of uniform characteristics in an environment of controlled conditions with a controlled supply of nutrients and feed water, each container comprising one or more plants and each plant or container being associated with a machine-readable identification that distinguishes the plant or container from other plants or containers;
  (b) a transporter system comprising a plurality of co-extensive storage transporters and a transfer conveyor, wherein a storage transporter provides support for a row of several containers, wherein each storage transporter comprises a belt which is moved by a motor, and wherein the belt of the storage transporter can be pulled back or forth by the motor allowing the transport of containers to or from the storage transporter;
  wherein the transfer conveyor is adjacent to an end portion of a storage transporter and cooperates with the storage transporter;
  (c) one or more motors associated with the transporter system, where the end of the storage transporter communicates with the transfer conveyor allowing containers to be transported back and/or forth from storage transporter to storage transporter and back and/or forth to specific areas in the array;
  (d) a continuous system for digital imaging of a plant comprising a transporter system for moving one or more plants at one or more intervals during its growing cycle through the system for digital imaging while the plant is being turned and imaged in a controlled manner, a belt mechanism for turning the containers in a controlled manner, and one or more digital imaging devices; and
  (e) a computer apparatus for analyzing images and/or information obtained from the digital images and/or information taken with the one or more digital devices of one or more characteristic of the plant while the plant is being moved through the digital imaging system.

In another embodiment, the present invention relates to a method for developing marketable information for improved plant breeding, which comprises
  (a) providing a plurality of plants growing under controlled environmental conditions, each plant being associated with a machine-readable identification that distinguishes the plant from other plants;
  (b) reducing the influence of micro-environment variations on the phenotype of the plants by moving the plants in an automated transporter system at one or more intervals during their growing cycle so as to avoid extended exposure to a particular micro-environment, thereby;
  (c) continuously transporting one or more plants at one or more intervals during its growing cycle through an imaging system containing a turning mechanism for turning the plant or the imaging device in a controlled manner;
  (d) taking images of one or more characteristic of the plant while the plant is being moved through the imaging system and storing the images on a computer or processing device;
  (e) analyzing the images for the one or more characteristic of the plant by computer processing and associating the resulting information with the machine-readable identification information for the plant; and
  (f) analyzing the resulting information for the one or more characteristic of the one or more plant;
  (g) wherein the images and/or resulting information provide marketable information for making decisions on plant identification and/or selection in a plant breeding system.

The invention further relates to a method for collecting data on a selected plant phenotype for rapid analysis of the effect of a genetic modification on the selected phenotype, which comprises
  (a) providing a plurality of plants growing under controlled environmental conditions, each plant being associated with a machine-readable identification that distinguishes the plant from other plants;
  (b) reducing the influence of micro-environment variations on the phenotype of the plants by moving the plants in an automated transporter system at one or more intervals during their growing cycle so as to avoid extended exposure to a particular micro-environment, thereby;
  (c) continuously transporting one or more plants at one or more intervals during its growing cycle through an imaging system containing a turning mechanism for turning the plant or the imaging device in a controlled manner;
  (d) taking images of one or more characteristic of the plant while the plant is being moved through the imaging system and storing the images on a computer or processing device;
  (e) analyzing the images for the one or more characteristic of the plant by computer processing and associating the resulting information with the machine-readable identification information for the plant; and
  (f) analyzing the resulting information for the one or more characteristic of the one or more plant; and
  (g) collecting the information from steps f) and/or g) on a selected plant phenotype for rapid analysis of the effect of a genetic modification on the selected phenotype.

BRIEF DESCRIPTION OF THE DRAWINGS

FIG. 3A shows a top view and FIG. 3B shows a side view.

FIGS. 4A and 4B represent an embodiment of the seed dehulling system where the movement between recipient and block is by rotation. FIG. 4A depicts the system with the recipient rotating and FIG. 4B with the block rotating.

FIG. 10 shows a dual magnet extraction system for molecular compounds.

DETAILED DESCRIPTION OF EXEMPLARY EMBODIMENTS OF THE INVENTION

Figure 1:
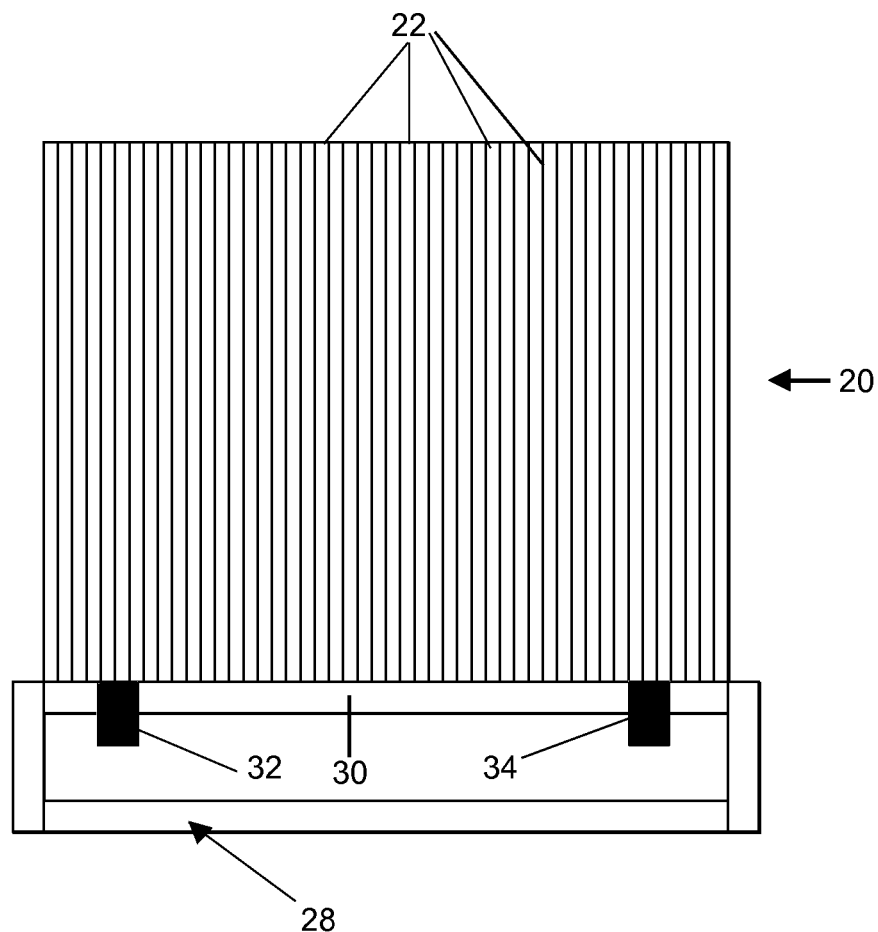
FIG. 1 is a schematic representation of the transporter system of the illustrative apparatus.

The present invention provides for a plant breeding system for high throughput analysis of genetic traits in plants. The present invention also includes surprisingly efficient methods for measuring the impact of genetic modifications on plants and employing the data for selecting plants with genetic modifications of interest and for selecting the best performing candidates. The methods provide for automated, high throughput analysis of plant phenotype and plant genotype in a breeding program.

For breeding to be successful, a sufficient number of genetic alterations has to be examined in order to identify the few amongst many that are of agronomic relevance.

The procedure for selection of genotypes has to be sufficiently discriminative for detecting phenotypic differences between the different genotypes and requires as a basis a set of parameters that is sufficiently detailed as to adequately describe the observed phenotypes.

The present systems and/or methods allow for evaluation and selection of genetic modifications in a surprisingly efficient manner and on a much larger scale (providing the ability to process thousands to ten of thousands of genetic modifications in a year) than traditional plant breeding evaluation and selection systems conducted under field or controlled conditions.

Even in a controlled environment or greenhouse setting when plants are grown on a defined substrate with controlled water and nutrient supply, environmental conditions still vary with geometrical locations within the greenhouse. This environmental variation can be due to differences in distance between plants and the proximity or otherwise to devices used for climate control and nutrient/water delivery, for example heating elements, cooling elements, windows, doors, misting devices, ventilators, water inlets and water outlets. In one aspect of the invention, environmental variations are significantly reduced through automated handling and by changing the location of growing plants in a greenhouse or controlled environment.

Another aspect of the invention provides an improved imaging system which significantly increases the throughput of the system while maintaining accuracy.

The present invention further provides an improved process for breeding plants in which plant breeding may be conducted using smaller seed quantities than in conventional breeding processes. Another aspect of the invention relates to an improved method for processing and/or analyzing seed in preparation for growing or after selecting plants with a genetic modification of interest.

The present system in another aspect relates to improved extraction and isolation of DNA for characterizing the genotype of plants or seeds in preparation for growing in the system or after selecting plants with a genetic modification of interest.

Plant Material

The present system is highly adaptable to various crop species, including those of large size and morphological complexity. According to one aspect of the invention, the plant subject to the breeding process is a self-pollinating plant, such as rice. A self-pollinating plant is one in which, under normal conditions, the female organs of any one given plant species are pollinated by pollen produced in the male organs of that same plant species.

According to another aspect of the invention, the plant subject to the breeding process is an open pollinating plant species, such as corn. An open pollinating plant species is a plant which is substantially a non-self pollinating plant species. With regard to corn, there are particular advantages associated with the use of plants which are relatively small or short and fast cycling which have a comparatively short cycle time, preferably about four months or less. These plants may be different varieties, hybrids, an inbred or a population, such as Gaspe or any inbred line derived from Gaspe e.g. through a number of generations of selfing.

Plant subjects can be other self-pollinating and non-self pollinating crop species, including but not limited to wheat, barley, rye, sorghum, canola, soybean, oats, sugarcane, sugarbeet, sunflower, tobacco, cotton, alfalfa, and flax.

In another aspect of the invention, the present system relates to the breeding of transgenic plants. The breeding of transgenic plants involves the introduction of at least one nucleic acid into a single plant by use of recombinant technology. Different plants may have the same or different nucleic acids introduced therein. Examples of methods of plant transformation are well known in the art and include, but are not limited to, *Agrobacterium*-mediated transformation and particle-accelerated or "gene gun" transformation technology. Nucleic acids can be incorporated into recombinant DNA constructs capable of introduction into and replication in a host cell. Such a construct can be a vector that includes a replication system and sequences that are capable of transcription and translation of a polypeptide-encoding sequence in a given host cell. A number of vectors suitable for stable transformation of plant cells or for the establishment of transgenic plants have been described. Transformed plants cells can be regenerated to whole plants by known methods. Transgenic plants are then grown and evaluated to identify plants having desirable traits. Transgenic plants can be compared to other transgenic plants and/or to corresponding control plants which do not contain the introduced nucleic acid. Plants having such desirable traits may be further evaluated in a field environment or may be backcrossed with different varieties of inbred lines of the same crop species or may be used to generate or test hybrids or may be used for the production of seed, possibly for commercial use.

*Agrobacterium*-mediated plant transformation is one of the most widely used methods for transferring genes into plants. *Agrobacterium* is a naturally occurring pathogenic bacteria found in the soil that has the ability to transfer its DNA into a plant genome. According to another aspect of the present invention, there is provided an improved method for the transformation of a monocotyledonous plant, especially of the family Gramineae, preferably rice. The improved method relates to an improvement of the *Agrobacterium*-mediated plant transformation method described in European patent application EP1198985, the contents of which are incorporated herein by reference.

Nowadays, *Agrobacterium*-mediated transformation of monocotyledonous plants is routinely performed; a technique once thought to be restricted to the transformation of certain dicotyledonous plants (flowering plants with two cotyledons in their seeds and broad leaves) such as potato and tomato. Monocotyledonous plants, or monocots, are flowering plants with one cotyledon in their seeds and narrow leaves with parallel veins, such as maize and rice.

*Agrobacterium tumefaciens* is a common soil bacterium that naturally inserts its genes into plants. In the process, the *Agrobacterium* causes plant tumors commonly seen near the junction of the root and the stem, deriving from it the name crown gall disease. *Agrobacterium*-mediated plant transformation uses this natural phenomenon to its advantage as a means for the introduction of foreign genes into a plant.

*Agrobacteria* are characterized in that, when a plant is infected therewith, a T-DNA region which is present on the plasmids that *Agrobacteria* have (e.g., Ti plasmid or Ri plasmid) is incorporated into the plant. The *Agrobacterium* transformation technique utilizes the incorporation of the T-DNA region into plants as a means for introducing genes into plants. In short, a plant is infected with an *Agrobacterium* which contains a desired recombinant gene. After infection, a desired recombinant gene is transferred from the *Agrobacterium* into plant cells so as to be incorporated into the plant genome.

It is known in the art that the efficiency of T-DNA transfer via *Agrobacterium* to a plant can vary depending on the tissue used for the transformation. For example, various protocols for *Agrobacterium*-mediated transformation of plants rely on callus transformation, immature embryo transformation, leaf, shoot apices, roots, hypocotyls, cotyledons, seeds and calli derived from various parts of a plant. In other methods, the transformed tissue is not removed from the plant but left in its natural environment, thus, the transformation takes place in planta.

It would be advantageous to find a fast and efficient method for the transformation of monocotyledonous plants, especially in the case of economically important crop plants, such as rice, corn, wheat, barley that constitute staple foods for much of the world's population.

Accordingly, there is provided a method for the transformation of a monocotyledon, comprising the steps of:

(i) Introducing into green seed *Agrobacterium* comprising a gene of interest;

(ii) Growing the seed to produce a transgenic plant comprising said gene of interest.

The term green seed as referred to herein is a seed that is in increasing order of preference about 15, 16, 17, 18, 19, 20, 21, 22, 23, 24, 25, 26, 27, 28, 29 or 30 days after pollination.

The terms "monocotyledonous plant(s)" or "monocot(s)" are used interchangeably herein to refer to flowering plants with one cotyledon in their seeds and narrow leaves with parallel veins. Preferably, the monocot is of the family Poaceae (Gramineae), which include grains, such as rice, wheat, maize, and other economically important crop plants. According to a preferred feature of the present invention, the plant to be transformed is rice (*Oryza sativa*). The methods of the invention are applicable to all rice varieties, although the methods were found to be particularly advantageous for indica rice varieties.

According to a preferred feature of the present invention, the green seed of a monocotyledonous plant is transformed using *Agrobaterium tumefaciens*.

Expression vectors suitable for expression of a gene of interest in plants, and tools and techniques for making the same, are well known in the art. The term "gene of interest" refers to any gene obtained from any source, or artificially synthesized, which is to be introduced into a plant. The gene of interest may be endogenous to the monocotyledonous plant to be transformed, for example a gene obtained from rice may be transformed into rice. The gene of interest may also be an antisense sequence of a target endogenous gene.

The gene of interest is operably linked to a promoter for expression of the gene of interest in the monocotyledonous plant. The promoter may be native to the gene of interest (endogenous promoter) or it may be from another source (exogenous promoter).

The expression vector may also comprise a selectable marker gene to facilitate the selection of transformed plants. Drug resistance genes such as a hygromycin phosphotransferase (HPT) gene for imparting hygromycin resistance, and a neomycin phosphotransferase II (NPTII) gene for imparting kanamycin resistance, are examples of selectable markers. A promoter is also operably linked to the selection marker to allow expression of the selectable marker gene.

A terminator sequence may also be present in the expression vector. The terminator sequence is located downstream of a region of a gene and encodes a protein involved in the termination of transcription when DNA is transcribed to mRNA, as well as the addition of a polyA sequence. Non-limiting examples of terminators include CaMV35S terminator and the nopaline synthetase terminator (Tnos).

Enhancers may also be used in the expression vector to enhance the expression efficiency of a target gene.

The green seed as hereinbefore defined is infected with the *Agrobacterium* to introduce the gene of interest into a plant. After removing the husks of the green seed of a plant to be transformed, the seed is pre-cultured in an intact state. A green seed being "intact" means that the seed has not been subjected to any artificial manipulation, such as removal of the ovule or scarring of the blastodisk.

In the pre-culture, the green seeds are sown on a medium (e.g., an N6D medium) containing an appropriate concentration of auxin (e.g., 2,4-D), and may be incubated for typically 4 to 5 days, and preferably 5 days. The pre-culture is completed before the seed tissue enters into a regeneration process. The temperature during the pre-culture is typically 25° C. to 35° C., and preferably 27° C. to 32° C. After completing the pre-culture, the seeds are sterilized and then washed thoroughly with water. The seeds are then infected with *Agrobacterium* under aseptic manipulation.

During the *Agrobacterium* infection (co-culture), the seeds are incubated in the dark, typically for 2 to 5 days, and preferably for 3 days. The temperature at this time is typically 26° C. to 28° C., and preferably 28° C. Next, in order to eliminate the *Agrobacterium* in the medium, the seeds are subjected to a treatment with an appropriate bacteria eliminating agent (e.g., carbenicillin). The transformed seeds are selected on the basis of a selection marker (e.g., drug resistance such as hygromycin resistance).

After the culture under appropriate bacteria-eliminating conditions and selection conditions, the selected transformed seeds are placed in a regeneration medium (e.g., an MS medium) containing appropriate plant regulatory substances, and incubated for an appropriate period of time. In order to allow a plant body to be regenerated, the regenerated transformant is placed on a rooting medium (e.g., an MS medium containing no plant regulatory substances). After the growth of roots is confirmed, the transformant may be potted.

It can be confirmed by using well-known techniques whether or not a desired recombinant gene has been introduced into a plant. This confirmation may be made, for example, via Northern Blot analysis. Specifically, the entire RNA is extracted from a leaf of a regenerated plant, subjected to electrophoresis on agarose in denatured condition, and thereafter blotted on an appropriate membrane. By allowing a labeled RNA probe which is complementary to a portion of the introduced gene to hybridize with the blots, the mRNA of the gene of interest can be detected. Alternatively, in the case where controlling the expression of an endogenous gene in the plant is desired via the introduction of a desired recombinant gene, the expression of the target endogenous gene may be tested for example, via the aforementioned Northern Blot analysis. If the expression of the target endogenous gene is significantly suppressed as compared to its expression in a non-transformed control plant, it is confirmed that the desired recombinant gene has been introduced into the plant and that the desired recombinant gene has acted to control the expression.

Conventional methods usually require a period of 3 to 4 weeks for inducing regeneration prior to *Agrobacterium* infection. In contrast, the method according to the present invention does not require a step of inducing regeneration, so that the number of days required for creating transformation monocotyledons can be reduced. Furthermore, according to the method of the present invention, it is also possible to reduce the period which is required for selection by conventional techniques, so that it is possible to reduce the influences of culture variation.

Recombinant DNA techniques which can be used in one aspect of the invention are known in the art and are described, for example, in Sambrook (2001) Molecular Cloning: a laboratory manual, 3rd Edition Cold Spring Harbor Laboratory Press, CSH, New York (hereby incorporated by reference in entirety) or in Volumes 1 and 2 of Ausubel et al. (1994), Current Protocols in Molecular Biology, Current Protocols (hereby incorporated by reference in entirety). Standard materials and methods for plant molecular work are described in Plant Molecular Biology Labfase (1993) by R. D. D. Croy, published by BIOS Scientific Publications Ltd (UK) and Blackwell Scientific Publications (UK) (hereby incorporated by reference in entirety).

Other aspects of the invention relate to the breeding of non-transgenic plants. In the breeding of non-transgenic plants, the creation of genotypic variation relies on the production of genetic alterations that can be obtained by techniques including recombination through classical crossing, chemical mutagenesis, radiation-induced mutation, somatic hybridization, inter-specific crossing and genetic engineering. The obtained plants can be compared to other non-transgenic plants, to transgenic plants, and/or to corresponding control plants. Following the creation of genotypic variation, selection of those genotypes having the most desirable agronomic phenotypes is performed.

Phenotype Evaluation

The phenotype (based for example on observations of growth habit, yield potential and resistance to stresses) is the result of contribution from the genotype itself (genotype-associated phenotype) and from the environment (environment-associated phenotype). The environment-associated phenotype is influenced by variations in the growth environment caused by variations in, for example, temperature, humidity, light, nutrient and water supply. An important factor that obscures phenotype-driven selection of desired genotypes is variations in the environment-associated phenotype component.

The invention therefore provides in one of its aspects a process for breeding plants which comprises growing plants of a species in an array of containers charged with growing medium of uniform characteristics in an environment of controlled climatic conditions with controlled supply of nutrients and feed water and changing the positions of the containers within the environment as required to ensure at least substantially uniform exposure of all plants in the containers to conditions in the environment.

A process according to the invention results in various significant and unexpected advantages. It enables effective dampening of environmental variations that influence the phenotypes of plants and therefore interfere with the selection of desired genotype-associated phenotypes. By changing the location of plants during their life cycle they are exposed to slightly different environmental settings at each location. When the displacement of all the plants in the breeding population occurs at a sufficiently high frequency (e.g. once per day or once per week) then the spatial effects are found to be randomized over the population. The dampening of environmental contribution to the phenotype of plants during breeding enables desired genotypes to be selected more reliably. The step of identifying the phenotype (such as without limitation growth, yield or stress tolerance) is facilitated by changing the location of plants. For example, where the plant phenotype is evaluated by means of appropriate equipment, the plants may be moved at appropriate intervals to the station where the equipment for evaluation is located. Enhanced uniformity of the environment for growing plants allows use of a smaller plant population for study, which in return reduces costs. The practice of the present invention allows for the breeding of various agronomic characteristics, such as enhanced yield and stress tolerance, using unexpectedly smaller plant population (typically on a greenhouse scale) compared to conventional methods requiring much larger plant populations (typically on a field scale) in order to accurately assess the phenotypic variation associated with different genotypes. The process enables surprisingly more efficient plant breeding. Given a fixed number of genetic alterations that can be studied and fixed level of required discriminative power, the size of the population representing a certain genetic alteration can be reduced because of the capacity to reliably establish phenotypes under conditions of limited availability of seeds (as is often the case in the generation following the creation of genetic alterations). The discrimination power of the present system thus reduces the need for extensive seed propagation and consequent loss of time.

The advantages inherent in being able to conduct a breeding process with smaller seed quantities than is possible employing methods of the prior art is particularly relevant in the case of breeding of transgenic plants for various desirable phenotypic characteristics (traits).

A process according to the invention preferably comprises identifying phenotype characteristics such as growth, yield and tolerance to biotic and abiotic stress of the plants at one or more intervals in the growing cycle. Preferably, the characteristics comprise one or more of an observable physical manifestation of the plant, color, greenness, yield, growth, biomass, maturity, flowering, nutrient use, water use, or effects of disease, pests, and/or stress. In an alternative preferred embodiment, the characteristics comprise one or more of leaf area, height, width, leaf angle, number of leaves, presence and/or number of inflorescences, number of shoots, and branching pattern. Yield can be evaluated by measuring, for example, plant height, leaf area, seed size, seed weight, seed number, size of seed heads (including ear size in maize), number and size of fruit, presence, number and size of inflorescences, and root area, size, and morphology. Biotic stress can be caused, for example, by bacterial, fungal, or viral disease, insects, and nematodes. Abiotic stress can be caused, for example, by heat, drought, cold, wind, high salinity, and low nutrient levels. Plants can be grown under low nutrient levels to evaluate the use efficiency of specific compounds such as, for example, nitrogen and phosphorous. Plants can also be evaluated for water use efficiency. The effects of biotic and abiotic stress can be evaluated directly, by measuring leaf color and morphology or an observable physical manifestation, or indirectly through measurement of growth characteristics such as, for example, plant height, leaf area, plant morphology, and/or yield. Phenotypic evaluation can be conducted through digital imaging systems of various parts of the plants. Image analysis can provide measurements of or an indication of, for example, plant height, leaf area, height of the gravity centre of the biomass, root area, greenness index, presence and/or number of panicles/inflorescence.

If desired, algorithms may be used to select and evaluate the information and the results statistically analyzed to identify plants with genetic modifications of interest, for selecting the best performing candidates or for selecting candidates having any given characteristics for any given further process, and/or identifying trait leads. In a preferred embodiment, the images and/or information are taken of above ground plant parts and/or of plant roots. Preferably, the above ground plant parts comprise shoots, leaves, tillers, inflorescence, flowers, seed, or any combination thereof.

In another embodiment, various measurements of one or more plant characteristics are conducted at one or more intervals during the life cycle of the plant. Measurements over time allow for calculations, for example, of maximum plant height, maximum leaf area, length of the growth cycle, emergence vigor, time to flowering, greenness before flowering. If stress has been applied, parameters such as greenness after stress, biomass reduction through stress, can additionally be calculated. Tools and techniques for making such measurements are well known in the art.

In one embodiment, the present methods and/or system can be used and/or adapted as necessary for determining the start of flowering and/or anthesis on an individual plant basis, for example, by measuring the reproductive structures of plants from images of these structures and deducing the start of flowering and/or anthesis from the measurements and average growth rates, such as described in WO 2007/093444, hereby incorporated herein by reference in its entirety.

Preferably, the evaluation occurs in a high throughput fashion. The high throughput system surprisingly allows for greater numbers of plants to be processed and evaluated compared with traditional greenhouse evaluation systems.

Preferably also, plants are selected for further breeding, for breeding or advancement experiments, or for commercial use by comparing the phenotype characteristics of the plants.

Plant Identification

In order for the inventive breeding system to run in a reliable, efficient and unattended way, plants can be identified by automation devices. Identification of plants in the horticultural industry is a common practice. The most widely used identification systems are either colored labels, text-printed labels or bar-coded labels. As automated transporting systems become more sophisticated, the need increases for a system that accurately provides an on-line overview on where plants (or plant batches) are standing in the greenhouse, the historical positioning and/or handling of the plants, and/or characteristics of those plants.

In one aspect of the invention, plants (or plant batches) are identified with a unique identifier. The unique identifier of each container and the information derived from each plant may be unambiguously linked to this identifier in a computer apparatus. Preferably the information is stored as such (information on a particular plant linked to the identification tag of the plant) in a digital database.

The invention provides in one of its aspects an apparatus suitable for use in conjunction with a container in which one or more plants is growing and having associated with it a device for receiving an enquiry signal and automatically responding by transmitting a unique identifier signal. The apparatus comprises
  (a) a transporter system by which a container may be supported for moving a container,
  (b) a device for transmitting the enquiry signal,
  (c) a device for recording the identifier signal as a digital output and
  (d) a computer apparatus to which the digital output is supplied for storage of the data in prescribed format in a database for manipulation to afford comparison of data related to the container.

In the apparatus according to this aspect of the invention, the enquiry and identifier signals are preferably radio signals although other forms of communication are within the scope of the invention including but not limited to identification through the use of barcode readers (1D, 2D) or identification through visual (camera) recognition of characters, numbers or signs.

Conveniently, the device for receiving an enquiry signal and automatically responding by transmitting a unique identifier signal consists of a copper coil, which acts as a small antenna and a chip, which stores information, such as described in U.S. Application Publication No. 2004/0200145, hereby incorporated herein by reference in its entirety. Such devices are hereinafter referred to as transponders. This form of apparatus embodies a warehousing system for plants (for example in a greenhouse) that provides an on-line overview of the location of individual plants in the array of plants. The principle of the system is that each plant container is labeled with a transponder and that these transponders are read by transponder readers positioned along the transporting system. The information on the geographical location of the readers together with the identity of the transponders that pass by the readers permit an overview of the position of the plants in the greenhouse.

The transponder information can also be used for correlating the historical positioning of the plants throughout the system, handling of the plants (such as nutrient or water supply, or through various digital components of the system), and/or correlating characteristics of the plants obtained in the various components of the system. The transponder information can be correlated preferably by a computer apparatus.

Automated Transporter Apparatus

The invention provides growing plants of a species in an array of containers charged with growing medium of uniform characteristics in an environment of controlled climatic conditions with controlled supply of nutrients and feed water and changing the positions of the containers within the environment as required to ensure at least substantially uniform exposure of all plants in the containers to conditions in the environment.

In a process according to invention, the positions of the containers may be changed continuously or at intervals. In one preferred process, they are changed to an extent and at intervals pre-set by an operator in accordance with observation of growth characteristics of the plants. The positions of the containers within the environment may be changed at intervals of up to two weeks, preferably from six hours to two weeks, more preferably at intervals from one day to one week. Preferably the positions of the containers within the environment may be changed in an automated way or automatically. One preferred apparatus supports an array of containers in the form of pots containing plants. Preferably there is one plant growing in each pot, although plants can be grown with several individuals in a pot or in trays or in a tray consisting of physically connected pots.

Apparatus suitable for use in a process according to the invention preferably comprises a transporter system upon which the containers are supported in a horizontally disposed uniform array, such as the system described in U.S. Application Publication No. 2006/0150490, hereby incorporated herein by reference in its entirety. In one embodiment, the transporter system comprises a plurality of co-extensive storage transporters each comprising a "U" shaped gutter equipped with a belt lying flat on the bottom of the gutter, and a transfer conveyor. In another embodiment, the belts are moved in the gutters by means of motors such as electric motors. In one embodiment of the apparatus hereinafter described, shuttle robots are provided which can position themselves in front of a particular gutter, and a motor in the robot can be activated to pull the belt in the gutter back or forth, thus allowing the transport of containers in and out of the gutters. The ends of the gutters communicate with the transfer conveyor, so that containers may be transported back and forth from gutter to gutter and back and forth to specific areas in the array. Preferably, the motors are caused to move the containers continuously or at time intervals; for example, at intervals from six hours to two weeks, more preferably at intervals of one day to one week. Thus, a storage transporter may be moved by a motor to move the row of containers supported on that storage transporter towards a first transfer station at which an endmost container of the row is transferred to the transfer conveyor, the transfer conveyor may be operated to move a container supported on it to a second transfer station and the motor of a second storage transporter may be operated to collect the container.

In a process according to the invention the containers are positioned as closely together as practicable bearing in mind the volume occupied by the plant or plants in the container.

Figure 2:
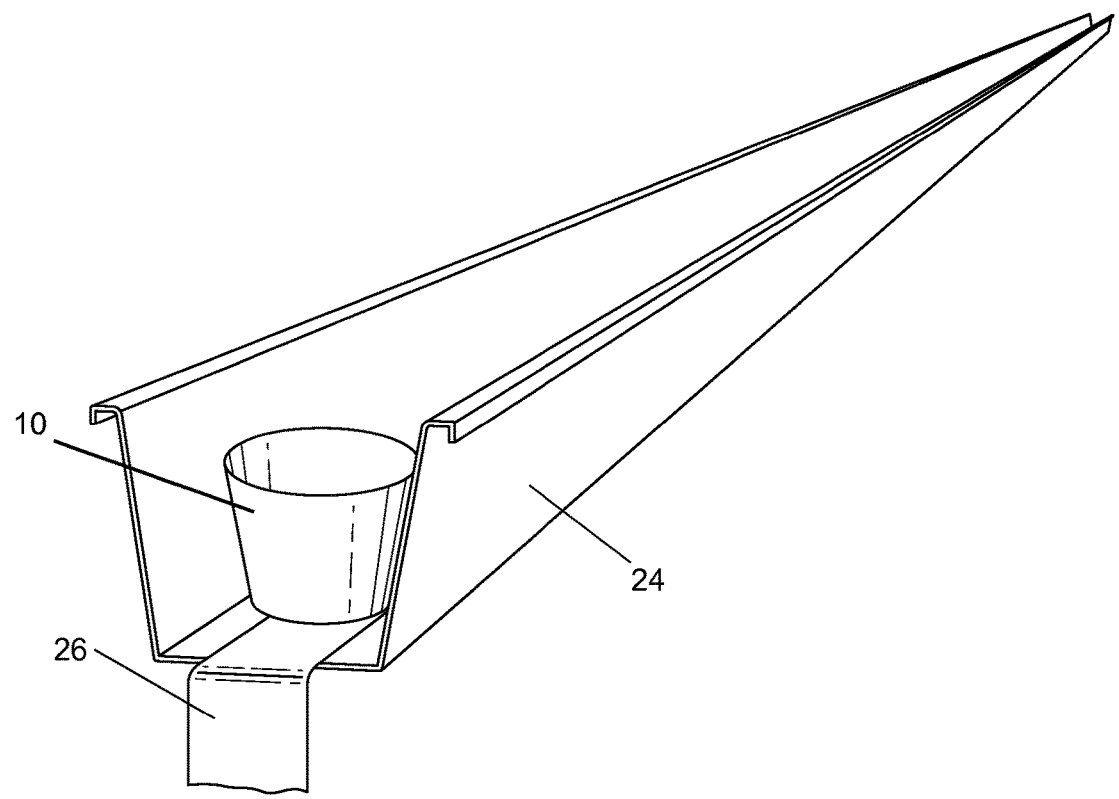
FIG. 2 is a view in perspective of a channel member and conveyor belt of the transporter system supporting a plant pot.

The illustrative apparatus depicted in FIGS. 1 and 2 is suitable for use in conjunction with a plurality of containers in the form of plant pots (10) (FIG. 2) in which one or more plants is growing in a medium selected for the purpose.

The apparatus comprises a transporter system (20) by which the pots are supported and moved as desired (FIG. 1). The transporter system (20) comprises a plurality of co-extensive storage transporters (22) each providing support for a row of several pots, the storage transporters being disposed adjacent one another to support rows of pots in a horizontally disposed array. Each storage transporter (22) comprises a channel member provided by a rigid "U"-shaped gutter (24) secured in parallel relation next to adjacent gutters. An endless belt (26) operates within each gutter (FIG. 2) and is located with an upper surface lying in the gutter and arranged to be drawn along it. Each belt (26) supports a row of closely spaced pots (10). The gutters (24) are situated with their end portions proximate to a belt conveyor (30) of transfer conveyor (28) located transversely to the gutters (24).

Electrically operated shuttle robots (32, 34) are employed to actuate movement of the belts (26) in the gutters (24). The movement causes the pots to be transported to or from the belt conveyor (30). A motor is provided for moving the belt conveyor (30) continuously. When a belt (26) is moved in its gutter in one direction, the row of pots supported on that belt is moved towards a transfer station at which an endmost pot of the row is transferred to the belt conveyor (30). When moved in the other direction the belt (26) moves the row of pots supported on that belt away from the belt conveyor (30), allowing space for a pot to be introduced to the end of that row. Each shuttle robot (32, 34) is arranged for movement along the belt conveyor (30) so that it may communicate with the gutters individually as desired. They are of similar construction and comprise guide members (not shown) for guiding pots moving along the belt conveyor (30). A cylinder of a pneumatically operated piston and cylinder device (not shown) is mounted on the shuttle robot between the guide members and its piston is arranged for movement horizontally across and above the belt conveyor (30). In its rest position, the piston serves to arrest a pot delivered from a gutter by its belt (26). When it is desired to remove a pot from the belt conveyor (30), the piston is actuated to push the pot and urge it into the selected gutter (22).

Historical positional data combined with fertilizer, watering and any other relevant data enables an operator of the apparatus to keep track of the nutritional regime of every single plant in the array. The information also enables the operator to schedule all plant movements in the most efficient way.

The apparatus is arranged so that the shuttle robots are actuated in response to data contained in the database so as to move a pot from one location to another.

Plant Imaging System

Another aspect of the system comprises a workstation or imaging system at which one or more imaging operations is performed on the plant or plants in the container.

Because of the asymmetric shape of many plants, images of plants from several angles are desirable. Many systems exist that turn plants around on a fixed turntable or rotating plate while being photographed. One aspect of the present invention relates to an improved mechanism that surprisingly gives absolute precision on the turning movement and plant location while the plants are being moved at high speed through the imaging system. Preferably the movement of the plants through the system is continuous.

One aspect of the invention relates to a digital imaging system, made to image plants while the plants are being moved and turned at the same time to be able to take images of all sides of the plant and store them in digital format.

In another embodiment, the imaging device is rotated, rather than the plant, to take images of the plant from different angles, while the plant is being moved continuously through the system.

Figure 3A:
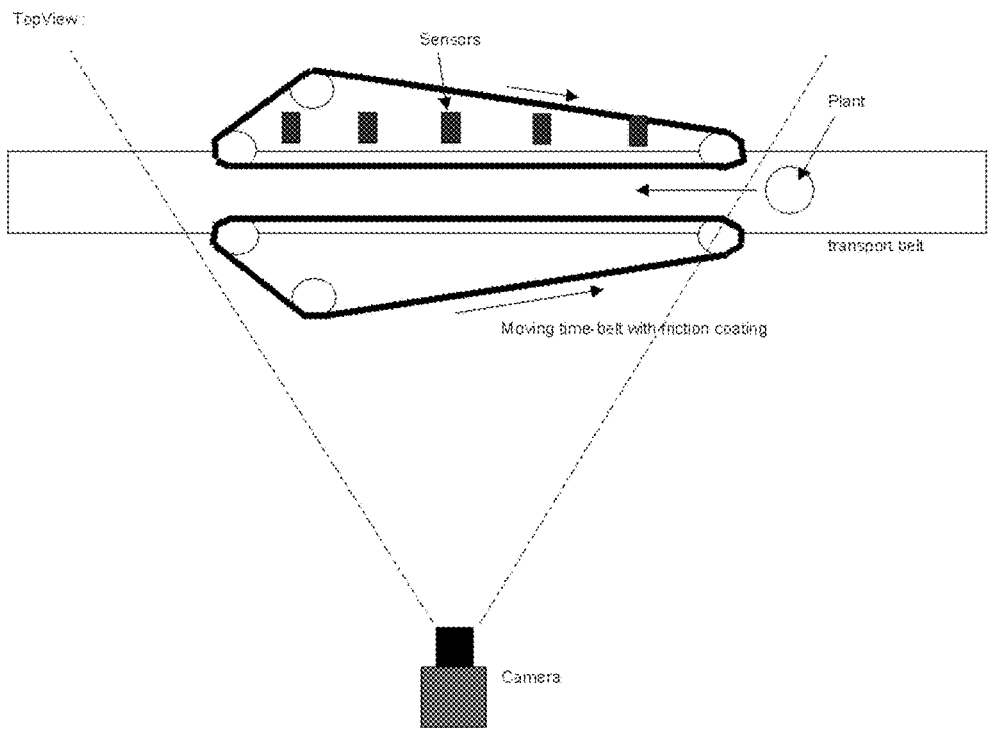
FIGS. 3A and 3B represent the imaging system showing the belt turning mechanism.
Figure 3B:
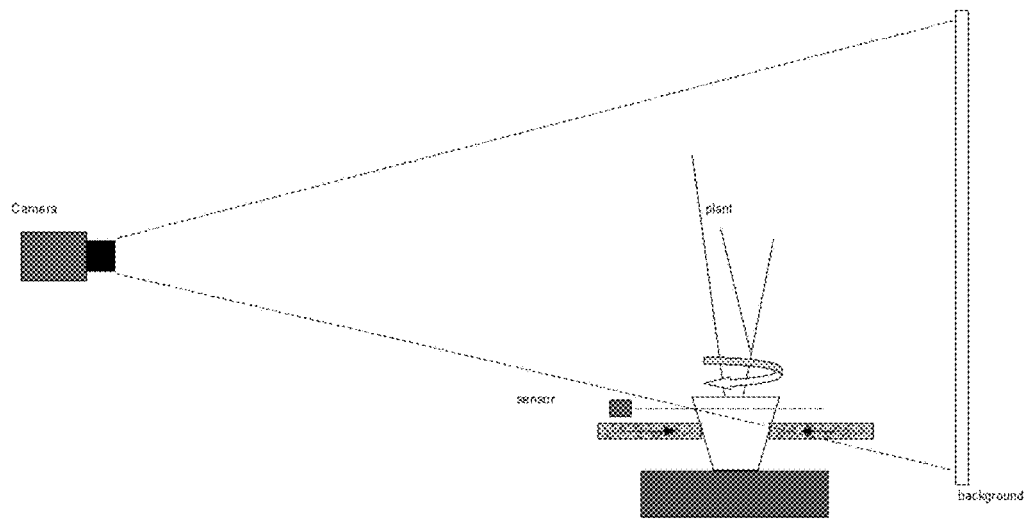

The apparatus comprises a transporter system by which a container or a pot containing a plant is moved through an imaging cabinet. Plants are moved on transport belts with speed controllers to assure a constant speed. Plants are moved on a transporter system at one or more intervals during its growing cycle through an imaging system in a continuous fashion. In one embodiment, the plants are being turned and imaged in a controlled manner, wherein the continuous system for imaging comprises a turning mechanism and an imaging device. The turning mechanism can comprise time-belts (see FIGS. 3A and 3B). The time-belts and/or the container can be coated with high friction material.

Friction can be characterized by a coefficient of friction. The coefficient of friction is a dimensionless quantity symbolized by the Greek letter p and is used to approximate the force of friction (static or kinetic): $\mu=F/N$. A high friction material corresponds to a coefficient of friction of about 0.6 or more. Examples of suitable high friction materials are described below. High friction materials can be composed of, but not limited to, for example polyurethane or various types of rubber such as ethylene-propyrene rubber (EPDM), an acrylonitryl-butadiene rubber (NBR), a chloroprene rubber (CR), a butadiene rubber (BR), a styrene-butadiene rubber (SBR), a butyl rubber (IIR), an isoprene rubber (IR), and a natural rubber.

When the plant reaches the imaging cabinet, the sides of the containers or pots are gripped between two time-belts (depicted for example in FIGS. 3A and 3B), that are preferably coated with a foamy, high friction material to assure a firm grip. The friction is sufficient to allow adequate gripping and rotating of the container or pot. The time-belts are positioned in order to grip the sides of the container. The position of the time-belts can be varied in order to accommodate various size containers. The belt mechanism and time-belts can be used with any type of pot or container material and can be adapted to any size pot or container. The speed of the time-belts is accurately controlled, preferably, by frequency inverters or frequency controlled motors. When the two time-belts have a different speed setting, the containers start to turn in a controlled way while being transported over the belt. Along the turning trajectory, in one aspect of the system several sensors can be installed to detect the containers and/or to trigger the imaging device.

In a preferred embodiment, the plants move continuously through the system without the need to remove the plant from the transporter system onto a separate turning plate for imaging then repositioning the plant back onto the transporter system or to stop the plant for imaging. This allows for increased throughput through the imaging system compared with conventional start and stop systems.

In another embodiment, the cameras may be rotated as the plant is being moved on the transporter belt through the imaging system.

In a preferred embodiment, the imaging device is a high speed and/or high resolution camera. More than one camera may be used in the system. The camera may be a high speed camera capable of taking high resolution pictures within 75 msecs. The camera may be a high resolution model larger or equal to 4 MegaPixel. Preferably the imaging device is a digital imaging device, but can also include infra red, near infra red, x-ray, and fluorescence imaging devices, such as for chlorophyll fluorescence, or infra red for leaf temperature.

Various imaging devices are known in the art and available from several providers, for example, Qbit, Walz, Hansatech, Photon-Systems-Instruments, LEMNATEC, REGENT, VISSER, ARIS, and FLIER.

The imaging cabinet preferably is shielded from natural daylight. Light inside the imaging cabinet is provided by a standardized set of lamps of which the light intensity can be controlled. In a preferred embodiment, high power and high frequency lighting is used to provide short exposure times to maintain accuracy of imaging since the containers are being moved in a continuous flow through the system.

Images taken in the imaging system can be processed on-line using imaging analysis software to extract information on the plants (e.g. height of the plants on the images, number of green pixels, estimation of root biomass etc.) and the processed data as well as the images get linked to the transponder tag unique identifier and downloaded to the computer.

In another embodiment of the apparatus, transmission of the identifier signal by the transponder of the container presented at the workstation actuates the imaging device for performing the operation. A transponder reader antenna can be mounted in such a way that it only reads the transponder of a container going through the imaging system. The reader of the transponder sends a signal to the software system that controls digital cameras in the imaging cabinet and thus activates the cameras to take a series of pictures.

In one embodiment, more than one image is captured, preferably 2, 3, 4, 5, 6 or more images are taken. In another embodiment, six high resolution color pictures are taken, for example, 24-bit×4 mega-pixel. In another aspect, for high throughput, within less than 5 seconds, 1-10, 2-8, 4-6, or about 6 images are taken, a background quality check is performed, necessary plant measurements are taken and the images are stored. In a further embodiment, industrial imaging software is used which is optimized for speed of processing, which can include the use of one or more computers or processors for processing, wherein the processing can include, but not limited to, parallelization or parallel processing on more than one computer, preferably using 2, 3, 4 or more computers or processors.

The imaging device described above could be combined with other automation devices such as for instance a "sorting device" that sorts plants according to parameters derived from the digital images (e.g. plant height). Other automation devices could perform particular actions on transponder-tagged plants and such actions (e.g. pruning, harvesting, packaging, destruction etc.) could be differentiated according to the information linked in a database to the transponder tag of the container in which the plant is growing. This apparatus is capable of operating in an unattended and fully automated way although manual operation or partial automation of one or more components, especially of pilot scale facilities. It may be used in the phenotyping of plants for breeding purposes. Thus, plants with particular morphological parameters that can be derived from digital images may be selected from a population of plants with different genetic constitution. The apparatus may be used without human intervention, and plants may be imaged at a high throughput rate, thus allowing not only imaging of a large population of plants in a short period of time, but also repeated imaging of the same population of plants so that evolution of the parameters over time may be recorded, both of which are desirable in plant breeding. Information derived from the digital images is collected for each individual plant from the population, and stored to allow for downstream data analysis. The unique identifier of each container and the information derived from each plant may be unambiguously linked to this identifier in the computer apparatus. Preferably the information is stored as such (information on a particular plant linked to identification tag of the plant) in a digital database.

Plant Root Evaluation Another aspect of the invention relates to a method for evaluating plant roots by growing plants in a substantially transparent container charged with a particulate, non-transparent growing medium and evaluating plant roots through the substantially transparent container by an imaging system, for example by digital imaging. The invention also provides an apparatus for evaluating plant roots, which apparatus is particularly suitable for evaluating, in a high throughput fashion, the roots of plants growing in a greenhouse. The system described in U.S.

Application Publication No. 2007/0289211, hereby incorporated herein by reference in its entirety, can be adapted as necessary and used in the present system for imaging and evaluation of roots.

The substantially transparent container may be a pot, tray, or the like. Preferably the container is a classical plant pot molded of transparent material, such as a suitable plastics material. It is preferred to have one plant per pot. The transparent material preferably contains a (green) pigment to absorb substantially all wavelengths of light except those between 500 and 600 nanometers. This serves to suppress the light avoidance response of the roots and to avoid algal growth on the inner walls of the pots. In use, plant roots may be seen against the walls of the container. The container may consist substantially entirely of transparent material or may have only a transparent bottom.

The particulate, non-transparent growing medium may be any soil-like substrate (for example soil, compost, peat, sand, or the like, or a combination thereof). The use of a defined substrate such as potting soil or rock wool may further reduce variations caused by the heterogeneity of the soil. Furthermore, the growing of greenhouse plants on a defined substrate allows the amount of water and nutrients to be given to the plants to be controlled.

In one embodiment, plant roots are evaluated by digital imaging, which facilitates the handling of large samples (of the order of up to, for example, several tens of thousands). It is preferred that plants are evaluated in an automated fashion using at least one camera. The plants may be presented (sequentially) to fixed camera(s). The plants are retrieved (for example, from a location in the greenhouse or elsewhere) and the substantially transparent containers in which the plants are placed are presented sequentially to an imaging device arranged to record images of the roots.

The transparent containers prior to imaging may be cleaned, for example by washing or brushing, to remove dust, soil or condensed water from the sides and/or bottom surface of the pot so that image quality is improved. The container may be washed using a water basin and imaging apparatus as described in U.S. Application Publication No. 2007/0289211, hereby incorporated herein by reference in its entirety. In another embodiment, a stream of water may be applied to various parts of the container. In a further embodiment, the dust, soil, or debris may be removed from one or more parts of the container using one or more brushes or an air blowing device. In another embodiment, one or more brushes or an air blowing device may be employed to remove dust and debris from the imaging device.

In another aspect of the invention, the plants are moved from the transport belt onto a rotating plate and the plant is turned in front of the imaging device. In another aspect of the invention, the plants remain on the transport belt and are rotated by two time-belts coated with a high friction material as described above. In another embodiment, the cameras may be rotated as the plant is being moved on the transporter belt. The plants are then returned to their original location, or to another location, all substantially without human intervention. There may be some degree of human intervention in the step of selecting the plant or series of plants for evaluation, but this may also be automated or computerized. In another embodiment, a minimum of about 500 plants per hour may be evaluated. The transporter system for the plants is preferably a moving belt. Root traits to be evaluated include, but are not limited to, growth rate, root length and thickness, root branching, and root anchorage.

Seed Processing Another aspect of the invention includes an improved seed dehulling device comprising a container to hold the seed, or recipient, and a block which fits inside the recipient which surprisingly minimizes breakage of seed and is applicable for various types of seed (for example as depicted in FIGS. 4A and 4B). The bottom of the recipient and the surface of the block are made of a high friction material (see description above).

A high friction material corresponds to a coefficient of friction of about 0.6 or more. An example of a suitable high friction material is VULKOLAN 90 (Bayer AG), with 90 reflecting the hardness (shore) of the material. Other examples of high friction material are the following:

| linatex | $\mu = 1.1$ | shore = 35 |
| supergrip blue | $\mu = 0.8$ | shore = 30 |
| PVC blue | $\mu = 1.0$ | shore = 40 |
| Correx gum | $\mu = 0.9$ | shore = 40 |
| Porrol | $\mu = 0.8$ | shore = 10 |
| PU D15 | $\mu = 0.8$ | shore = 70 |
| Linatrile | $\mu = 1.0$ | shore = 55 |
| RP400 | $\mu = 1.0$ | shore = 35 |
| PVC white | $\mu = 1.1$ | shore = 40 |

The recipient is made to hold the desired amount of seed in a substantially single layer. The seed dehulling device also comprises a motor for moving the recipient or the block and a pressure system that causes a downward force to squeeze the seed between the recipient and the block. The movement of the recipient or block may include, but not limited to, rotating, rolling, or rubbing. Preferably, the recipient or the block is rotated, for example as depicted in FIGS. 4A and 4B. The device can be made in different sizes to hold the appropriate amount of seed, so that only one run needs to be performed to dehull all of the desired seeds. To operate the device, seeds are poured into the recipient, the motor is started, and pressure is applied to force down the block onto the seeds. A predefined pressure level and pressure cycling assure that the seeds are dehulled within a short timeframe, for example 2 to 20 seconds, with limited or no breakage. The device is stopped and the seed/hull mixture can be transferred to a cleaning device to separate seeds from hulls. The recipient and block are open systems that can be fully inspected to ensure that no seeds are left behind after dehulling, thus preventing contamination of seed batches. The recipient and block can be inspected visually or with an imaging device. The surfaces of both the recipient and the block are flat, thus minimizing breakage of the seed. The seed dehulling device is applicable for any form or shape of seed. The device can be used with minimal breakage of oblong seed, such as rice. Pressure on the seeds can be controlled and varied to optimize dehulling and minimize seed breakage. In one aspect of the invention, the rotating speed of the block and recipient and the force applied in the system can be controlled and varied. In a preferred embodiment, the speed of movement of recipient or block and pressure may be regulated or controlled automatically.

In a further aspect of the invention, seed can be automatically transported to or from the seed dehulling device. The transfer of the seed hulls and dehulled seed can be transported from the dehulling device to a system to separate seeds from hulls in an automatic and/or automated way. The system to separate seed hulls and dehulled seed can further comprise counting, imaging, and/or evaluating physical and/or biochemical parameters of the seed. The counting, imaging, and/or evaluating of the seed can also be done in an automatic or an automated way. This system can also include a device to perform physical tests or selective actions on the seed in order to assess or classify the dehulled seeds of that batch. Examples of uses for the seed dehulling system include, but are not limited to, improving germination of seed before planting and/or removal of the seed coat before seed analysis after harvesting.

The seed may be processed with the seed dehulling device after plants have been selected for a particular phenotype or a genetic modification or in preparation for growing plants prior to evaluation. Seeds may be further processed by methods known in the art, such as described in U.S. Pat. No. 7,367,458, which is hereby incorporated herein by reference in its entirety. Following dehulling, seed can also be analyzed for several different traits, including but not limited to fatty acid, protein, carbohydrate, and vitamin composition.

Figure 8:
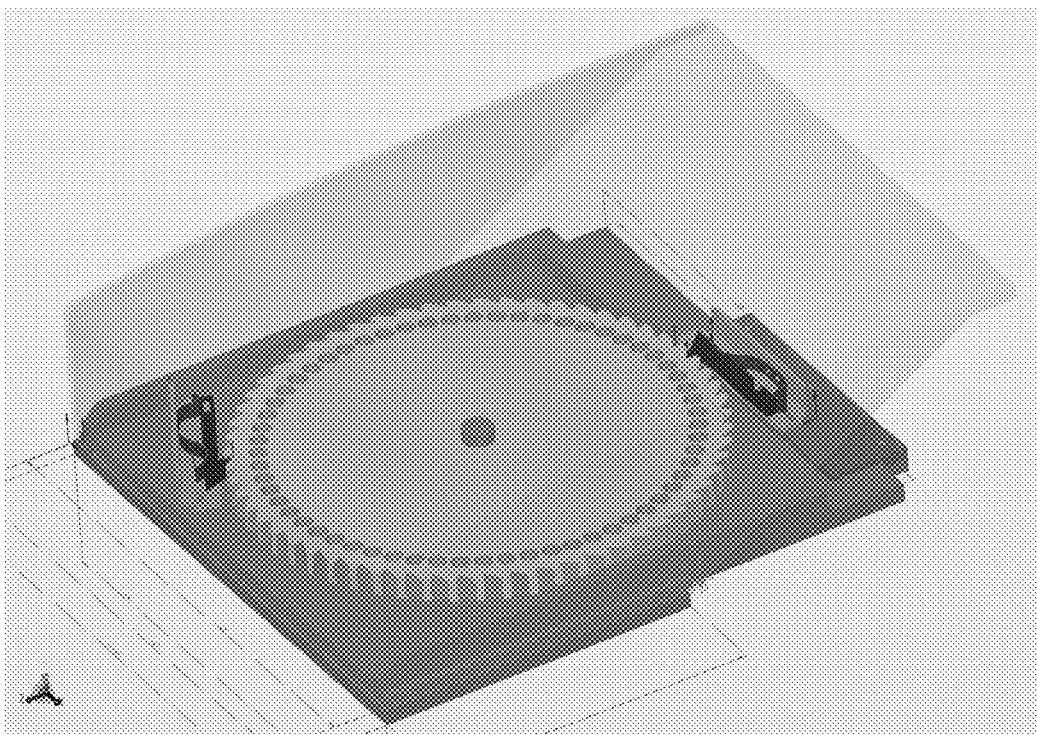
FIG. 8 depicts an autosampler disk.

In a further embodiment, an autosampler can be used which automatically inserts seed samples in analysis devices such as, but not limited to, a near infrared analyzer (NIR). An example of an autosampler is depicted in FIG. 8. When the device starts, it measures the vials one by one, moving this disk one position forward each time between the analyses. The number of samples to be analyzed corresponds to the number of holes in the sampling disk. The disk can be made or adapted with a different number of holes and thus holding a different number of vials and/or samples. The use of the autosampler in this fashion allows for the total number of samples held on the disk to be analyzed without the operator being present, in an automated or in an automatic way. Seed samples from seed to be used for planting, from seed obtained following growth and harvest of the plants grown in the greenhouse, and/or from dehulled seed obtained following processing through the dehulling device can be used.

For use with an NIR analyzer, a seed sample (for example, a sample of 25 seeds) is inserted in small glass vials with a flat bottom, which is preferred since the NIR measures from the bottom upwards. The vials are inserted in the holes of an autosampler disk, for example as depicted in FIG. 8. When the device starts, it measures the vials one by one, moving this disk one position forward each time between the analyses. The number of samples to be analyzed corresponds to the number of holes in the sampling disk, for example a disk with 60 samples is depicted in FIG. 8. The disk can be made or adapted with a different number of holes and thus holding a different number of vials and/or samples. The use of the autosampler in this fashion allows for the total number of samples held on the disk to be analyzed without the operator being present, in an automated or in an automatic way. The NIR can identify the seed vials by the use of sample lists made prior to inserting the sample vials, or by scanning a barcode or other machine-readable identification put on or associated with the vials. The results are automatically analyzed and the different biochemical compounds (such as fatty acids, protein, water, etc.) are dosed for each sample. These results can then be uploaded or entered into a database and used as one of the possible criteria for evaluating and/or selecting a gene of interest.

A Modified Sampling System for Extracting DNA.

Extraction of DNA from plant tissue is often necessary in a breeding program for evaluation of genotype. In preparation for DNA extraction, one embodiment provides for an improved sampling system. This sampling system consists of an improved way to form a reaction vial in which the steps needed to prepare the plant material for DNA extraction can be done on a improved multiwell format which minimizes the risk of sample to sample contamination (spill over) by using a double seal vial system. Another embodiment comprises the use of individually traceable tubes in a multiwell format to form an array of reaction vials in which the preparation steps for DNA separation can be performed.

Figure 9:
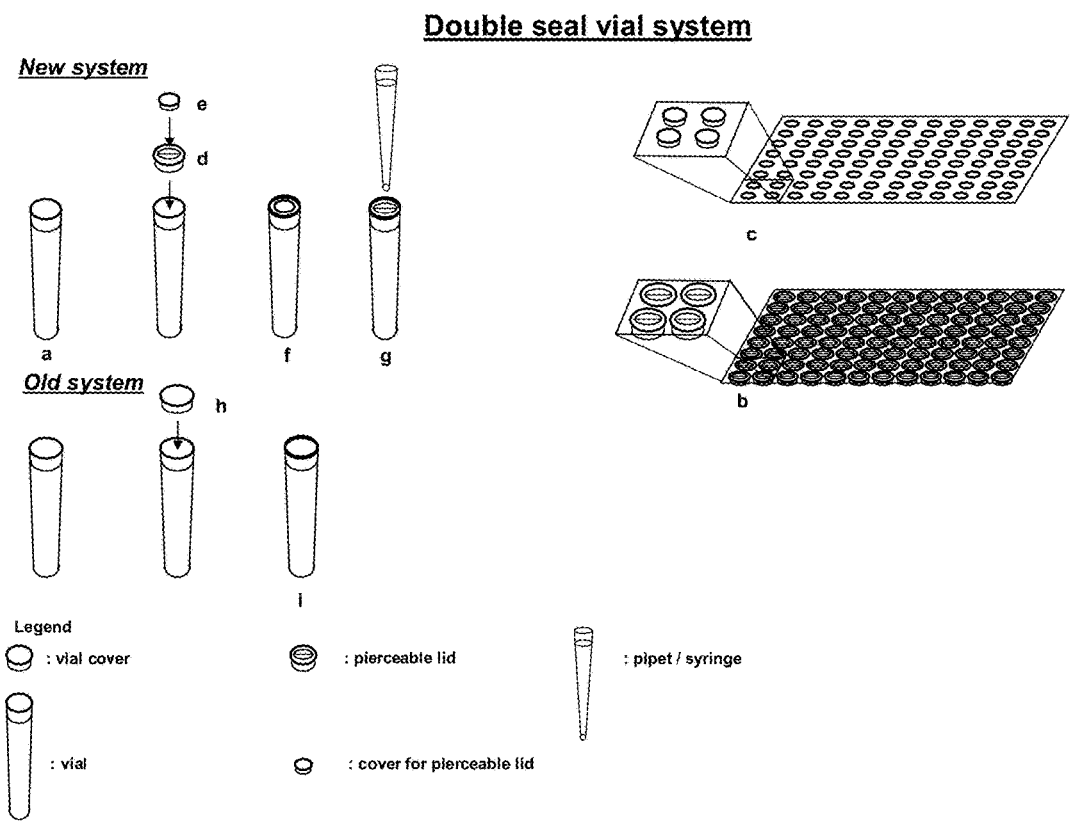
FIG. 9 depicts the double seal vial system.

Conventional reaction vials, such as depicted in FIG. 9 component (a), are usually containers that can be sealed (individually or by group) with caps that are solid (h). To be able to perform the different steps in molecular biology protocols, the reaction vials have to be opened (i.e. the lid has to be removed) to add and/or remove a component from the reaction vial. When the reaction vials contain individual or unique elements, the risk of spreading material from one vial to the next is eliminated by opening/closing the vials at different moments in time or by separating the vials far enough from one another. With vials arranged on a multiwell format it is not possible to avoid sample contamination when using individual caps. The present improved method comprises a double seal vial system which combines two cap mats (caps arranged in a multiwall format) (see FIG. 9, New system, b and c) to replace the conventional single solid cap (see FIG. 9, Old system, h).

The use of double caps for the vials is advantageous because it allows rapid access to the inside of the vials without opening the vials themselves through the removal of the second cap mat and the pierceable slit feature of the first cap mat. The pierceable slit also allows for working without vial to vial contamination and this in an array format. The combination of both caps gives rise to a cover that is solid enough to allow for "heavy duty" work with the vials, for example, grinding plant material at −80° C. with a solid bead, or incubation at higher temperature without loss of liquid through evaporation.

Another component of the multiwell system comprises an array of fixed tubes (for example, 96, 384, or 1536 wells) or loose individual tubes arranged in a rack. Individual tubes can be non-labeled or labeled. In a preferred embodiment, labeled tubes are used as traceable reaction vials. With the labeling of tubes, the sample keeps its identity obviating the need to give a new identity. By arraying labeled tubes in a matrix, not only the position of the well identifies the sample, but the sample keeps its unique identity independent of the position in one or other array. Thus, with a labeled tube, every time the tube or sample leaves the multiwell rack (for example, being taken to the next station in the synthesis/extraction process, such as an incubation station, etc.), the sample does not require a new identification (e.g. the position in the rack of the new station).

A DNA Extraction System

Extraction of DNA from plant tissue is often necessary in a breeding program for evaluation of genotype. One aspect of the invention relates to a method of DNA extraction from plant tissue comprising the use of magnetic beads and a double magnet system. This method increases the amount of DNA extracted per sample and therefore requires less plant tissue as starting material. This method also allows for increased concentration of DNA, reduced elution volumes, and increased purity resulting from improved contact of the magnetic beads with the elution buffer. The present improved double magnet extraction system in comparison with single magnet methods is depicted in FIG. 10.

The improved extraction system also provides for use of smaller buffer volumes since the beads are always attracted to the second magnet under the reaction vial.

This system can also be used with magnetic beads binding different molecular components depending on the binding affinity of the beads (for example, DNA, RNA, proteins, etc.).

All of the references disclosed herein are hereby incorporated herein by reference in their entireties.

EXAMPLES

The present invention will now be described with reference to the following examples, which are by way of illustration alone and are not intended to completely define or to otherwise limit the scope of the invention.

Example 1. Reduction in Environment-Associated Phenotype

In classical breeding it is good practice and in crop variety evaluation programs it is necessary to test new varieties in several locations and for several seasons. The reason for this is that phenotypes vary with changing environments and different rankings of varieties are obtained under different environments. The analysis of publicly available data of over 40 years of crop evaluation in wheat in Western Australia (Cullis et al., 2000, Journal of Agricultural Science, Vol. 135, pp. 213-222) and 10 years in oat in South Australia (Frensham et al., 1997, Euphytica, Vol. 99, pp. 43-56), indicate that season to season (i.e. weather conditions) is by far the most important factor in this environmental variability. Cullis et al. found that 89% of the environment variability in the wheat yield data is caused by season variability. Frensham et al. estimated this percentage at 82% for oat yield. This percentage is expected to be of a similar magnitude for all crops.

The genotype by environment interaction is a challenge in very early discovery programs. Early discovery programs cannot test over several seasons, so are dependent on a particular season and results are difficult to compare across seasons. Thus, to reduce environmental variability, stabilizing the climate should be the first target.

The invention provides growing plants of a species in an array of containers charged with growing medium of uniform characteristics in an environment of controlled climatic conditions with controlled supply of nutrients and feed water and changing the positions of the containers within the environment as required to ensure at least substantially uniform exposure of all plants in the containers to conditions in the environment.

Example 2. Increased System Throughput by Continuous System for Imaging

In conventional imaging systems, plants are stopped just before entering the vision unit and allowed to enter one by one. Plants could additionally be stopped, positioned on a rotating plate for imaging, then removed from the plate and repositioned and conveyed out of the imaging station one plant/container at a time. In the present system, plants do not stop but proceed in a continuous fashion through the imaging system. The plants are positioned with an appropriate distance between the plants to obtain the highest speed without causing mismatches during transponder reading and/or collisions. Mechanical and optical sensors are utilized to synchronize the plant transport and the imaging actions. Some standard optical sensors sometimes sensed hanging leaves as separate moving objects (i.e. a plant with hanging leaves was sensed as two or more plants). Optical sensors that could differentiate single leaves from whole plant were preferably used.

In conventional systems, the plant was placed next to a transponder reader and turned around until the transponder was read. Only then was the picture taken and the process was continued; therefore, the transponder reading was secured, but slow. In the present system, the plants pass by a transponder reader without stopping, so the time frame for successful reading is quite reduced. The reading conditions are optimized by appropriate modification, for example, of the type of transponder, size, number, distance and position of the reader relative to the path of the plants, or by minimizing interferences due to metal masses and electrical devices (such as belt motors). In addition, some checking algorithm is utilized to avoid mismatch of transponder identity, such as may occur when a transponder is not read or when two plants are too close when approaching the transponder reader for the reader to separately read the transponders.

In the imaging system, the plant was captured on more than one high resolution color picture such as a 24-bit×4 mega-pixel, preferably on 6 pictures, then a background quality check was performed, the necessary plant measurements were done, and the pictures stored, all within about 5 seconds or less, which time frame is short especially with such large color pictures compared to conventional systems. The successive steps are preferably maximally optimized for speed while retaining accuracy.

Preferably an industrial camera with the highest possible frame-rates is used.

Industrial imaging packages, optimized for speed, were operated on one or more computers or processors, which required special programming technique called "parallelization" (processes run in parallel on the more than one processors), preferably on a "quad-core" computer (4 parallel processors).

The continuous flow through the imaging system increased throughput and the amount of plants that were processed. The imaging accuracy was maintained while the plants were being moved and turned in a continuous fashion during imaging, as shown in FIG. 5.

Figure 5:
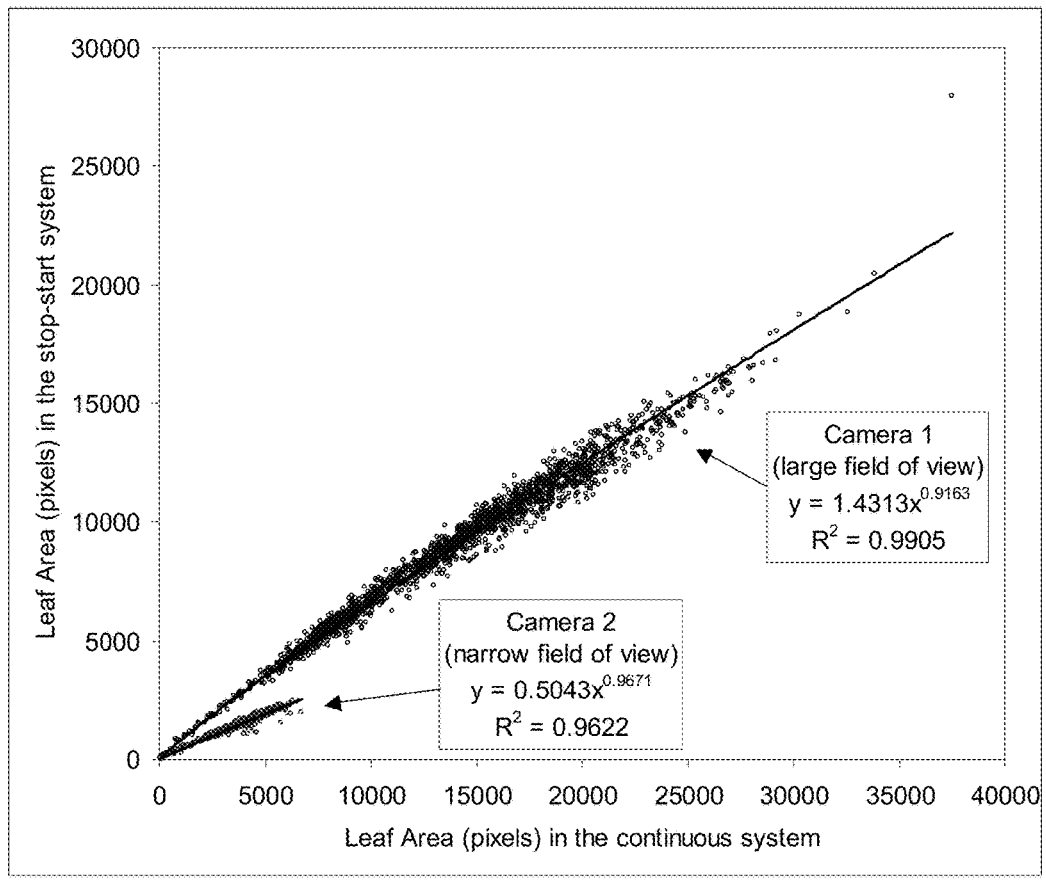
FIG. 5 shows the tight correlation between leaf area measured in the present continuous system versus the conventional stop-start system.

FIG. 5 shows the tight correlation between leaf area measured in the present continuous system versus the conventional stop-start system. The data set represents a population of 2500 plants that were imaged in the present system and in the conventional one on the same day. The difference between the conventional and the present measurement is on average 3%, which is similar to the variation observed between repeated measurements of the same plants in one or the other system.

Conventional systems usually use two cameras, one for young plants (i.e. camera 2, narrow field of view (FOV)) and one for plants older than 25 days (i.e. camera 1, large FOV). This was due to the lower resolution (1.2 mega-pixels) of the cameras in conventional systems, which required the use of a smaller field of view for young plants in order to reduce variability. The present system preferably has only one camera but with much higher resolution (for example, 4 mega-pixels), which allows measurement of young, small plants with the same accuracy as in the conventional system.

Figure 6:
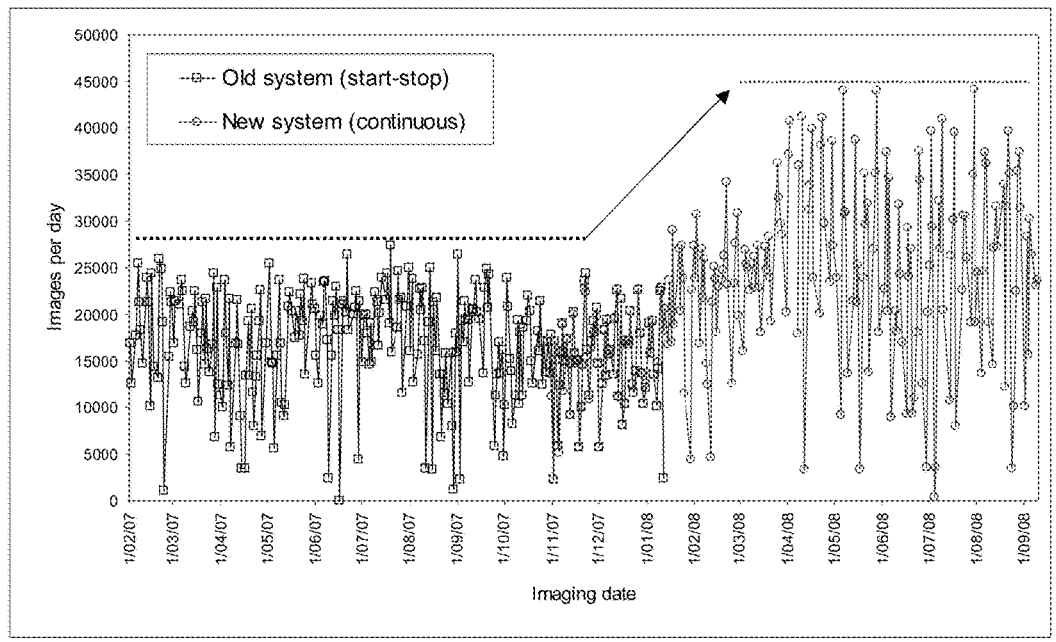
FIG. 6 shows the increase in daily imaging throughput following the implementation of the continuous system (new system) compared to conventional start-stop system (old system).

FIG. 6 shows the increase in daily imaging throughput following the implementation of the continuous system (new system) compared to conventional start-stop system (old system).

Example 3. Improved Seed Dehulling Device

An improved seed dehulling device was developed for efficient dehulling and to minimize seed breakage. An example of the device is depicted in FIGS. 4A and 4B.

Nipponbare seeds: 05OS0.000.311.754, were used and evaluated for breakage. Various parameters of pressure and time of applied pressure were tested. Seeds were placed in the recipient, the block was lowered with a lever into the recipient onto the seeds at a pressure measured on a scale placed below the recipient, and the lever was then released.

Table 1 shows the results of experiments (method) for different pressure and time parameters (# seeds+pressure) tested. Each experiment was conducted twice. The results depict average values.

| Method | Amount | Seconds | Pressure (kg) | Movement | Dehusked | Not dehusked | Broken |
|---|---|---|---|---|---|---|---|
| 1 | 150 | 10 | 2 | No | 97 | 52 | 1 |
| 2 | 150 | 15 | 2 | No | 109.5 | 40.5 | 0 |
| 3 | 150 | 20 | 2 | No | 120 | 30 | 0 |
| 4 | 150 | 10 | NA | Yes | 103.5 | 46 | 0 |
| 5 | 150 | 15 | NA | Yes | 117 | 33 | 0 |
| 6 | 150 | 20 | NA | Yes | 132.5 | 17.5 | 0 |
| 7 | 150 | 10 | 3 | No | 103.5 | 46 | 1 |
| 8 | 150 | 15 | 3 | No | 123 | 26 | 1 |
| 9 | 150 | 20 | 3 | No | 127 | 23 | 0.5 |
| 10 | 150 | 10 | 4 | No | 114.5 | 34.5 | 1.5 |
| 11 | 150 | 15 | 4 | No | 123 | 27 | 0.5 |
| 12 | 150 | 20 | 4 | No | 130 | 19 | 1 |

Figure 7:
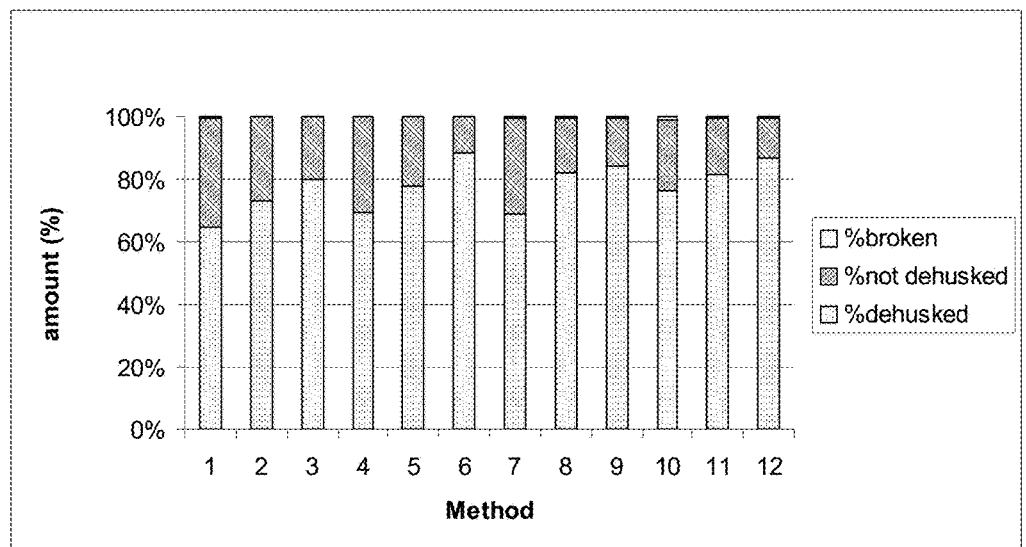
FIG. 7 shows the results for the different experiments/methods (# seeds+pressure) presented as percentage of dehulled seeds of the starting material.

FIG. 7 shows the results for the different experiments/methods (# seeds+pressure) presented as percentage of dehulled seeds of the starting material. As shown in FIG. 7, method 6 shows the greatest percentage of dehulled seed, where the lever was moved during 20 seconds up and down at a reasonable pace, applying alternately a pressure of from about 2-3 kg (as measured on the balance) and no pressure at all, and resulting in no seed breakage (see Table 1).

The seed used in the present dehulling device were usually dried before storage, thus making it even harder for dehulling without broken seeds.

Seed breakage of up to 20% can occur in conventional high volume dehusking/polishing machines. For machines which dehull smaller amounts of seed, breakage can occur between 2 and 10%. The seeds used in these conventional devices were usually non-dried seeds or seeds treated with vapor or other process which help loosen the hulls.

The dehulling device of the present invention thus provides an improved system with minimal breakage compared to conventional devices.

Example 4. Autosampler Device

An autosampler can be used which automatically inserts seed samples in analysis devices such as, but not limited to, a near infrared analyzer (NIR). An example of an autosampler is depicted in FIG. 8. Seed samples from seed to be used for planting, from seed obtained following growth and harvest of the plants grown in the greenhouse, and/or from dehulled seed obtained following processing through the dehulling device can be used.

For use with an NIR analyzer, a seed sample (for example, a sample of 25 seeds) is inserted in small glass vials with a flat bottom, which is preferred since the NIR measures from the bottom upwards. The vials are inserted in the holes of an autosampler disk, for example as depicted in FIG. 8. When the device starts, it measures the vials one by one, moving this disk one position forward each time between the analyses. The number of samples to be analyzed corresponds to the number of holes in the sampling disk, for example a disk with 60 samples is depicted in FIG. 8. The disk can be made or adapted with a different number of holes and thus holding a different number of vials and/or samples.

The use of the autosampler in this fashion allows for the total number of samples held on the disk to be analyzed without the operator being present, in an automated or in an automatic way. The NIR can identify the seed vials by the use of sample lists made prior to inserting the sample vials, or by scanning a barcode or other machine-readable identification put on or associated with the vials. The results are automatically analyzed and the different biochemical compounds (such as fatty acids, protein, water, etc.) are dosed for each sample. These results can then be uploading or entered into a database and used as one of the possible criteria for evaluating and/or selecting a gene of interest.

Example 5. A Modified Sampling System

In preparation for DNA or other molecular compound extractions, one embodiment provides for an improved sampling system. This sampling system consists of an improved way to form a reaction vial in which the steps needed to prepare the plant material for DNA extraction, for example, can be done in an improved multiwell format which minimizes the risk of sample to sample contamination (spill over) by using a double seal vial system.

Conventional reaction vials, such as depicted in FIG. 9 component (a), are usually containers that can be sealed (individually or by group) with caps that are solid (h). To be able to perform the different steps in molecular biology protocols, the reaction vials have to be opened (i.e. the lid has to be removed) to add and/or remove a component from the reaction vial. When the reaction vials contain individual or unique elements, the risk of spreading material from one vial to the next is eliminated by opening/closing the vials at different moments in time or by separating the vials far enough from one another. With vials arranged on a multiwell format it is not possible to avoid sample contamination when using individual caps. The present improved method combines two cap mats (caps arranged in a multiwall format) (see FIG. 9 b and c) to replace a solid cap (see FIG. 9, New system). The first cap mat (b) consists of an array of caps whereby the individual caps have a pierceable slit (d) through which liquid components can be added to and/or removed from the reaction vial. The second cap mat (c) consists of the same array layout with smaller individual caps (e) fitting inside the first cap mat. The combination of both caps (f) acts like a solid cap comparable to the prior situation (See FIG. 9, Old system).

The use of double caps for the vials is advantageous because it allows rapid access to the inside of the vials without opening the vials themselves through the removal of the second sap mat and the pierceable slit feature of the first cap mat. The pierceable slit also allows for working without vial to vial contamination and this in an array format. The combination of both caps gives rise to a cover that is solid enough to allow for "heavy duty" work with the vials, for example, grinding plant material at −80° C. with a solid bead, or incubation at higher temperature without loss of liquid through evaporation.

Another embodiment comprises the use of individually traceable tubes in a multiwell format to form an array of reaction vials in which the preparation steps for DNA separation can be performed.

Another component of the multiwell system comprises an array of fixed tubes (for example, 96, 384, or 1536 wells) or loose individual tubes arranged in a rack. Individual tubes can be non-labeled or labeled. In a preferred embodiment, labeled tubes are used that were originally designed as storage containers for chemical components and are presently used as traceable reaction vials. With the labeling of tubes, the sample keeps its identity obviating the need to give a new identity. By arraying labeled tubes in a matrix, not only the position of the well identifies the sample, but the sample keeps its unique identity independent of the position in one or other array. Thus, with a labeled tube, every time the tube or sample leaves the multiwell rack (for example, being taken to the next station in the synthesis/extraction process, such as an incubation station, etc.), the sample does not require a new identification (e.g. the position in the rack of the new station).

Example 6. Molecular Compound Extraction System

Extraction of DNA from plant tissue is often necessary in a breeding program for evaluation of genotype. One aspect of the invention relates to a method of molecular compound, such as DNA, extraction from plant tissue comprising the use of magnetic beads and a double magnet. DNA will be used as an example, but the method is also applicable to other molecular compounds. Advantages of the improved method is to increase the amount of DNA extracted per sample and therefore requiring less plant tissue as starting material. This method also allows for increased concentration of DNA, reduced elution volumes, and increased purity resulting from improved contact of the magnetic beads with the elution buffer. The present improved method in comparison with other methods is depicted in FIG. 10.

Some former methods also used magnetic beads for DNA binding. However, the beads were stationary in the reaction vials during the DNA extraction process (see FIG. 10, Old system). The different buffers in the extraction method were added to and removed from the same reaction vial in subsequent pipeting steps.

The improved method is based on the physical movement of beads to different reaction vials already containing buffers in the extraction protocol (see FIG. 10, New system). After binding of the DNA to the magnetic beads (a), attraction of the beads is done by a first magnet positioned inside a reaction vial lid (b). The reaction vial lid together with the beads is moved to a second reaction vial prefilled with buffer. Removal of the beads from the magnet inside the lid is done by attraction to a second magnet below the reaction vial (c). Once the beads are attracted to the second magnet the reaction vial lid with the first magnet can be removed (d). Once the reaction vial is removed from the second magnet the magnetic beads are free in a buffer (e) as in the original vial.

Other extraction systems make use of only one magnet in the vial lid (i), depicted in FIG. 10 as the Single magnet system. In the single magnet system, in order to remove the beads from the lid, the magnet is drawn away from the vial lid, which causes the magnetic beads to follow the magnet as high as possible on the vial lid (j). This is disadvantageous; because the magnetic beads attach to the lid at the extremity of the magnet (strongest magnetic field is found at the extremities). This final position on the vial lid in the single magnet system make it difficult for the beads to come in contact with the next buffer liquid, especially if the volumes of the subsequent buffer is less then the former (k), in contrast with the new system where the beads are at the bottom of the vial in the buffer from the attraction to the second magnet.

The new system also allows for using smaller buffer volumes where needed since the beads are always attracted to the second magnet under the reaction vial.

In another embodiment, the second magnet can be an electromagnet which is a permanent magnet.

The new system can be used with magnetic beads binding different molecular components depending on the binding affinity of the beads (for example, DNA, RNA, proteins, etc.).

In another embodiment, the extraction and identification of the molecular compound can be conducted on the seed either before the seeds are planted or after growth, imaging, and selection for a particular phenotype or genetic modification. Analysis prior to planting and imaging can be used as a pre-screen as an additional early selection tool based on gene expression of a gene of interest.

What is claimed is:

1. A plant breeding system for high throughput analysis of genetic traits in plants, comprising:
   (a) a first transporter system comprising a plurality of co-extensive storage transporters and a transfer conveyor adjacent to an end portion of the co-extensive storage transporters,
   wherein each storage transporter provides support for a row of several containers charged with growing medium of uniform characteristics, each container comprising one or more plants and each plant or container being associated with a machine-readable identification that distinguishes the plant or container from other plants or containers,
   wherein each storage transporter comprises a belt supporting the row of several containers, the belt being pulled back or forth by a motor allowing transport of the containers to or from the transfer conveyor;
   wherein the transfer conveyor cooperates with the storage transporters to allow the containers to be transported back and/or forth from one storage transporter to another storage transporter;
   (b) a continuous system for digital imaging of a plant comprising a second transporter system for moving one or more plants at one or more intervals during its growing cycle through the system for digital imaging while being turned and imaged in a controlled manner, a belt mechanism for turning the containers in a controlled manner, and one or more digital imaging devices,
   wherein the belt mechanism of the system for digital imaging comprises time-belts,
   wherein the time-belts and/or the containers are coated with a friction material having a coefficient of friction of about 0.6 or more,
   wherein the time-belts are positioned in order to grip the sides of the containers; and
   (c) a computer apparatus for analyzing digital images and/or information of one or more characteristics of the one or more plants taken with the one or more digital imaging devices.

2. The plant breeding system of claim 1, wherein the time-belts and/or the containers are coated with a friction material having a coefficient of friction of about 0.6 or more.

3. The plant breeding system of claim 2, wherein the belt mechanism of the system for digital imaging comprises frequency controlled motors actuate the time-belts.

4. The plant breeding system of claim 2, wherein the time-belts have different speed settings allowing the container to turn in a controlled way while being transported over the belts.

5. The plant breeding system of claim 1, where the position of a container containing a plant is detected by sensors which trigger the action of the digital imaging system.

6. The plant breeding system of claim 1, wherein the digital imaging system comprises one or more high speed and/or high resolution cameras.

7. The plant breeding system of claim 6, wherein the camera is capable of taking high resolution pictures within 75 milliseconds.

8. The plant breeding system of claim 1, wherein the storage transporters are disposed adjacent one another to support rows of containers in a horizontally disposed array.

9. The plant breeding system of claim 1, wherein the transfer conveyor comprises at least a first transfer station and a second transfer station, wherein the belt of the first storage transporter moves the row of containers supported on the first storage transporter towards the first transfer station at which an endmost container of the row is transferred to the transfer conveyor, and wherein the transfer conveyor is operated to move the container supported on it to the second transfer station to allow a second storage transporter to collect the container.

10. The plant breeding system of claim 1, wherein the one or more plants comprise one or more transgenic plants.

11. The plant breeding system of claim 1, wherein the one or more digital devices are arranged to record images and/or take information of above ground plant parts and/or of plant roots.

12. The plant breeding system of claim 1, wherein the machine-readable identification comprises a device for receiving an enquiry signal and automatically responding by transmitting a unique identifier signal wherein the enquiry and identifier signals are radio signals.

13. The plant breeding system of claim 1, further comprising a seed dehulling device for processing seed from a plant grown in a container or processing seed in preparation for growing the plant in a container comprising a recipient-block combination each having a flat surface with high friction on which the seeds are put, where either recipient or block is moved under pressure, in such a way to release the hulls and to minimize damage to the seeds.

14. The plant breeding system of claim 13, further comprising a pressure system to regulate or control the speed of movement of the recipient or block and pressure in an automated way.

15. The plant breeding system of claim 13, further comprising a motor to rotate, roll, or rub the recipient or block.

16. The plant breeding system of claim 13, further comprising a device to transport the seeds to or from the seed dehulling device in an automated way.

17. The plant breeding system of claim 13, further comprising a cleaning device to separate dehulled seeds from hulls.

18. The plant breeding system of claim 17, further comprising a device to count, image, and/or evaluate physical and/or biochemical parameters of the seed.

19. The plant breeding system of claim 18, wherein the device for counting, imaging, and/or evaluating the seed is an automated device.

20. The plant breeding system of claim 13, further comprising a device to inspect the recipient and block after the seeds and hulls are removed from the seed dehulling device to ensure that no seeds remain to prevent cross-contamination between batches of seed.

21. The plant breeding system of claim 1, further comprising a modified sample extraction system comprising a double seal vial system comprising one or more of a first cap comprising a pierceable slit and one or more of a second cap which fits inside the first cap for extracting DNA from seed, plants, or plant parts, from a plant grown in a container or in preparation for growing the plant in a container.

22. The plant breeding system of claim 1, further comprising a modified bead mediated isolation system for isolating DNA from seed, plants, or plant parts, from a plant grown in a container or in preparation for growing a plant in a container comprising magnetic beads which are capable of binding to a molecular compound, a first magnet positioned inside a reaction vial lid, and a second magnet positioned below the reaction vial.

* * * * *